United States Patent
Inui et al.

(10) Patent No.: US 12,006,527 B2
(45) Date of Patent: Jun. 11, 2024

(54) CORYNEFORM BACTERIUM TRANSFORMANT AND METHOD FOR PRODUCING 2-PHENYLETHANOL USING SAME

(71) Applicants: Research Institute of Innovative Technology for the Earth, Kyoto (JP); Sumitomo Bakelite Co., Ltd., Tokyo (JP)

(72) Inventors: Masayuki Inui, Kyoto (JP); Kazumi Hiraga, Kyoto (JP); Masako Suda, Kyoto (JP); Masayoshi Hashizume, Tokyo (JP); Junya Ishida, Tokyo (JP)

(73) Assignees: Research Institute of Innovative Technology for the Earth, Kyoto (JP); Sumitomo Bakelite Co., Ltd., Tokyo (JP)

( * ) Notice: Subject to any disclaimer, the term of this patent is extended or adjusted under 35 U.S.C. 154(b) by 269 days.

(21) Appl. No.: 17/414,021

(22) PCT Filed: Dec. 19, 2019

(86) PCT No.: PCT/JP2019/049921
§ 371 (c)(1),
(2) Date: Jun. 15, 2021

(87) PCT Pub. No.: WO2020/130095
PCT Pub. Date: Jun. 25, 2020

(65) Prior Publication Data
US 2022/0025412 A1    Jan. 27, 2022

(30) Foreign Application Priority Data

Dec. 20, 2018 (JP) .................... 2018-238497

(51) Int. Cl.
*C12P 7/22* (2006.01)
*C12N 15/77* (2006.01)
*C12R 1/15* (2006.01)

(52) U.S. Cl.
CPC .............. *C12P 7/22* (2013.01); *C12N 15/77* (2013.01); *C12R 2001/15* (2021.05)

(58) Field of Classification Search
CPC ......... C12P 7/22; C12N 15/77; C12N 9/0006; C12N 9/001; C12N 9/1085; C12N 9/1205; C12N 9/16; C12N 9/88; C12R 2001/15; C12Y 101/01027; C12Y 103/01013; C12Y 207/01071; C12Y 504/99005; C12Y 401/01043; C12Y 205/01054; C12Y 301/03; C12Y 402/01118
See application file for complete search history.

(56) References Cited

U.S. PATENT DOCUMENTS

2019/0119664 A1    4/2019 Inui et al.

FOREIGN PATENT DOCUMENTS

| CN | 104560852 B | 8/2017 |
| WO | 2011/057288 A2 | 5/2011 |
| WO | WO 2013/016724 * | 1/2013 |
| WO | 2016/094604 A1 | 6/2016 |
| WO | 2017/169399 A1 | 10/2017 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Shen et al., Journal of Bioscience and Bioengineering 122(1):34-39, 2016.*
Kogure et al., Metabolic Engineering 38:204-216, 2016.*
Ren et al., GenBank accession No. ADF63262 published Mar. 22, 2017.*
Ren et al., GenBank accession No. CP001918 published Mar. 22, 2017.*
Zhang et al., J Microbiol Biotechnol 40:643-651, 2013.*
Zhang et al., Journal of Industrial Microbiology and Biotechnology 42:787-797, 2015.*
Liu et al., World J Gastroenterol 10(24):3683-3687, 2004.*
Koma et al., Applied and Environmental Microbiology 78(17):6203-6216, 2012.*
Malhotra et al., GenBank accession No. ABF58692 published Mar. 27, 2008.*
Kwak et al., GenBank accession No. CP012914 published Nov. 6, 2015.*
Lucas et al., GenBank accession No. ACF02026 published Dec. 11, 2013.*
Lucas et al., GenBank accession No. CP001096 published Dec. 11, 2013.*

(Continued)

*Primary Examiner* — Delia M Ramirez
(74) *Attorney, Agent, or Firm* — Morgan, Lewis & Bockius LLP

(57) ABSTRACT

Provided is a microorganism that is able to produce 2-phenylethanol at a high concentration, and a method of efficiently producing 2-phenylethanol by using a saccharide as a raw material.
Provided is a coryneform bacterium transformant in which a shikimate pathway is activated, and further, a gene that encodes an enzyme having phenylpyruvate decarboxylase activity is introduced in such a manner that the gene can be expressed.
Also provided is a 2-phenylethanol producing method that includes causing the coryneform bacterium transformant according to the present disclosure to react in water containing a saccharide.

23 Claims, 2 Drawing Sheets
Specification includes a Sequence Listing.

(56) References Cited

OTHER PUBLICATIONS

Koga et al., "Purification and Characterization of Indolepyruvate Decarboxylase: A Novel Enzyme for Indole-3-Acetic Acid Biosynthesis in Enterobacter Cloacae," The Journal of Biological Chemistry, 267 (22): 15823-15828 (1992).

Liu et al., "Genome mining of 2-phenylethanol biosynthetic genes from *Enterobacter* sp. CGMCC 5087 and heterologous overproduction in *Escherichia coli*," Biotechnology for Biofuels, 11: 305 (2018).

Liu et al., "Metabolic engineering of *Escherichia coli* for the production of phenylpyruvate derivatives," Metabolic Engineering, 32: 55-65 (2015).

Extended European Search Report issued in corresponding European Patent Application No. 19900590.1 dated Sep. 28, 2022.

Kim et al., "Biosynthesis of 2-phenylethanol from glucose with genetically engineered Kluyveromyces marxianus," Enzyme and Microbial Technology, 61-62: 44-47 (2014).

Guo et al., "Metabolic engineering of *Escherichia coli* for production of 2-phenylethanol and 2-phenylethyl acetate from glucose," Journal of Agricultural and Food Chemistry, 66: 5886-5891 (2018).

Averesch et al., "Metabolic Engineering of the Shikimate Pathway for Production of Aromatics and Derived Compounds—Present and Future Strain Construction Strategies," Frontiers in Bioengineering and Biotechnology, 6 (32): 1-19 (2018).

Romasi et al., "Development of Indole-3-Acetic Acid-Producing *Escherichia coli* by Functional Expression of IpdC, AspC and IadI," Journal of Microbiology and Biotechnology, 23 (12): 1726-1736 (2013).

International Search Report issued in corresponding International Patent Application No. PCT/JP2019/049921 dated Mar. 24, 2020.

* cited by examiner

CORYNEFORM BACTERIUM TRANSFORMANT AND METHOD FOR PRODUCING 2-PHENYLETHANOL USING SAME

SEQUENCE LISTING SUBMISSION VIA EFS-WEB

A computer readable text file, entitled "SequenceListing.txt," created on Jun. 15, 2021 with a file size of 19,812 bytes contains the sequence listing for this application and is hereby incorporated by reference in its entirety.

TECHNICAL FIELD

The present disclosure relates to a technique for producing 2-phenylethanol. More specifically, the present disclosure relates to a *Corynebacterium glutamicum* transformant that has been subjected to a specific genetic manipulation so that a function of producing 2-phenylethanol should be imparted, and an efficient technique for producing 2-phenylethanol by using this transformant.

BACKGROUND ART 2-phenylethanol has a rose-like aroma, and is widely utilized in cosmetics, flavoring agents, perfuming agents, etc.

2-phenylethanol utilized industrially these days is produced by organic synthesis using crude oil as a raw material principally. On the other hand, very little 2-phenylethanol is extracted and produced from a plant raw material such as rose flowers, due to difficulties in securing enough raw materials and extraction efficiency.

In view of steep price rise and uncertain supply of crude oil, and with a view to the reduction of greenhouse gas emission for preserving the global environment, shift has occurred from crude oil to biomass raw materials, and environment-friendly fermentative production through a bioprocessing using microorganisms has attracted attention. For example, the yeast species *Kluyveromyces marxianus* has an Ehrlich pathway, thereby being capable of producing 2-Phenylethanol from phenylalanine, which is one of the amino acids.

However, phenylalanine that can be used a raw material is utilized as an essential amino acid as a food additive or a feed additive and is more expensive than a saccharide raw material such as glucose, which makes phenylalanine unsuitable for being industrially utilized as a raw material for the production of 2-phenylethanol.

Non-patent Document 1 reports that 1.3 g/L (about 11 mM) of 2-phenylethanol was produced from glucose by using a recombinant yeast that is obtained by using, as a host, the yeast species *Kluyveromyces marxianus* to which phenylalanine analog resistance has been imparted, that highly expresses a phenylpyruvate decarboxylase gene (aro10) and an alcohol dehydrogenase gene (adh2), and in which aroG (fbr) is introduced that encodes a feedback inhibition mutant of 3-deoxy-D-arabino-heptulosonate-7-phosphate (DAHP) synthase derived from the pathogenic bacteria *Klebsiella pneumoniae*.

Non-Patent Document 2 discloses the production of 2-phenylethanol from glucose using *Escherichia coli* into which the 2-keto acid decarboxylase (kdc) gene of the yeast species *Saccharomyces cerevisiae* is introduced. This document reports that about 8 mM of 2-phenylethanol was produced from glucose.

PRIOR ART DOCUMENT

Non-Patent Document

[Non-patent Document 1] Kim T Y, Lee S W, Oh M K. Biosynthesis of 2-phenylethanol from glucose with genetically engineered *Kluyveromyces marxianus*. Enzyme Microb. Technol. 61-62: 44-47(2014)

[Non-patent Document 2] Guo D, Zhang L, Kong S, Liu Z, Li X, Pan H. Metabolic engineering of *Escherichia coli* for production of 2-phenylethanol and 2-phenylethyl acetate from glucose. J Agric Food Chem. 66: 5886-5891(2018)

SUMMARY OF THE INVENTION

Problem to be Solved by the Invention

Against this background, it is desired that 2-phenylethanol is more efficiently produced from inexpensive saccharide raw material such as glucose. There are, however, problems that the pathway for biosynthesis of 2-phenylethanol from a saccharide raw material such as glucose is composed of more than several tens of steps, and is subjected to a variety of feedback regulations and transcriptional regulations. Additionally, strong cytotoxicity exhibited by 2-phenylethanol makes enhanced production by a biological method more difficult.

The present disclosure provides a microorganism that is able to produce 2-phenylethanol at a high concentration, and provides a method of efficiently producing 2-phenylethanol by using a saccharide as a raw material.

Means to Solve the Problem

The present disclosure, in one aspect, relates to a coryneform bacterium transformant in which a shikimate pathway is activated, and further, a gene that encodes an enzyme having phenylpyruvate decarboxylase activity is introduced in such a manner that the gene can be expressed.

The present disclosure, in another aspect, relates to a 2-phenylethanol producing method that includes causing the coryneform bacterium transformant according to the present disclosure to react in water containing a saccharide.

Effect of the Invention

According to the present disclosure, in one or a plurality of embodiments, 2-phenylethanol can be efficiently produced from a saccharide by using a coryneform bacterium.

MODE FOR CARRYING OUT THE INVENTION

Figure 1:
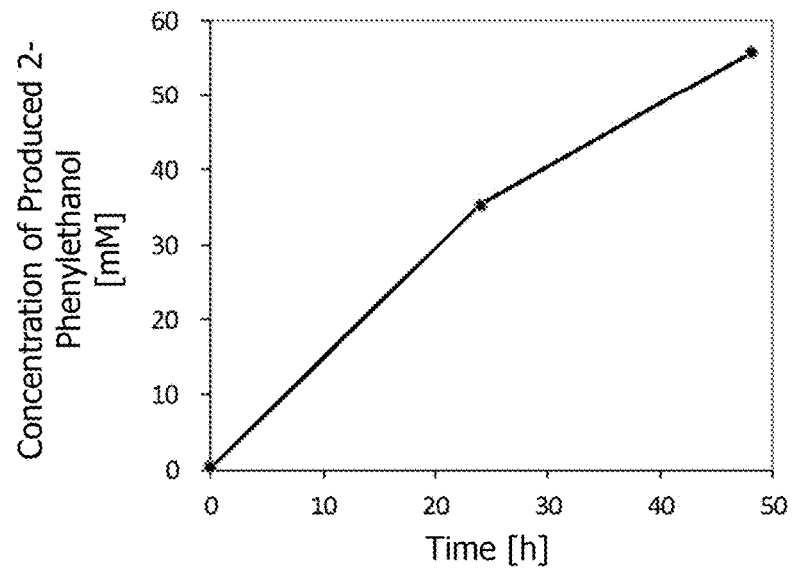
FIG. 1 shows the production of 2-phenylethanol under aerobic culture conditions.

The present inventors have found that the coryneform bacterium has more excellent resistance against 2-phenylethanol as compared with *Kluyveromyces marxianus*, *Escherichia coli*, or *Pseudomonas putida* S12 known as a solvent-resistant bacterium. By using the coryneform bacterium as a host, enhancing the shikimate pathway in the coryneform bacterium and introducing a phenylpyruvate decarboxylase gene into the same, they arrived to the creation of a coryneform bacterium transformant capable of performing the enhanced production of 2-phenylethanol from a saccharide raw material, and the enhanced production of 2-phenylethanol using this coryneform bacterium transformant.

The following describes the present disclosure in detail.

(I) Transformant Having Ability to Produce 2-Phenylethanol

The transformant according to the present disclosure, in one aspect, is a coryneform bacterium transformant obtained by activating a shikimate pathway, and further introducing a gene that encodes an enzyme having phenylpyruvate decarboxylase activity into a coryneform bacterium as a host in such a manner that the gene can be expressed. With the transformant according to the present disclosure, 2-phenylethanol can be produced.

In the present disclosure, the method for gene introduction into the coryneform bacterium may be the introduction of a plasmid, or the incorporation into the genome.

Host

The coryneform bacterium used as a host is, in one or a plurality of embodiments, *Corynebacterium glutamicum*. *Corynebacterium glutamicum* is a group of microorganisms defined in Bergey's Manual of Determinative Bacteriology, Vol. 8, 599 (1974).

More specifically, *Corynebacterium glutamicum* is, for example, the strain of *Corynebacterium glutamicum* R (FERM BP-18976), ATCC13032, ATCC13869 (DSM1412), ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), or MJ-233AB-41 (FERM BP-1498). Among them, strains R (FERM BP-18976), ATCC13032, and ATCC13869 (DSM1412) are preferable, among which the strain R (FERM BP-18976) is further preferable.

According to molecular biological classification, names of some species of coryneform bacteria, such as *Brevibacterium flavum, Brevibacterium lactofermentum, Brevibacterium divaricatum*, and *Corynebacterium lilium* are standardized to *Corynebacterium glutamicum*, and these are therefore encompassed in the present disclosure.

In addition, in the coryneform bacterium as a host, a by-product production pathway of a 2-phenylethanol production pathway is preferably blocked with a view to improving the production of 2-phenylethanol. Further preferably, an entirety or a part of the ldh (lactate dehydrogenase) gene, the qsuB (3-dehydroshikimate dehydratase) gene, the hdpA (dihydroxyacetone phosphatase) gene, and the cgR #1237 gene (phenylalanine uptake transporter) are disrupted.

Still further, the coryneform bacterium as a host preferably has reduced consumption of phosphoenolpyruvate (PEP) from the same viewpoint, and more specifically, the ptsH (phosphoenolpyruvate-dependent sugar phosphotransferase system) gene, which is one of the subunits of the glucose uptake transporter is preferably disrupted, with the iolT1 (Myo-inositol facilitator) gene being expressed instead. Further preferably, lolT1 highly expresses an enzyme gene of glucokinase (either ATP-dependent glucokinase or polyphosphate-dependent glucokinase, or both of these) for phosphorylating glucose taken into cells.

Phenylpyruvate Decarboxylase (pdc) Gene

Phenylpyruvate decarboxylase (EC4.1.1.43) is an enzyme that catalyzes a reaction of producing phenylacetaldehyde from phenylpyruvate. Indole 3-pyruvate decarboxylase (EC4.1.1.74), or branched-chain 2-oxo acid decarboxylase (EC4.1.1.72), can be suitably applied to the production of 2-phenylethanol as long as it can catalyze the present reaction.

In one or a plurality of embodiments, examples of the gene encoding the enzyme having phenylpyruvate decarboxylase activity include ipd (Indole-3-pyruvate decarboxylase) C, kivd (α-ketoisovalerate decarboxylase), kdc (alpha keto acid decarboxylase) A, aro10 (phenylpyruvate decarboxylase), and pdc (pyruvate decarboxylase).

The gene is not limited particularly, and may be derived from microorganisms, plants including roses, or animals. From the viewpoint of the productivity of 2-phenylethanol, the gene is preferably an ipdC gene, more preferably an ipdC gene of the bacteria of the genus *Enterobacter* or an ortholog thereof, and further preferably an ipdC gene of *Enterobacter cloacae* or an ortholog thereof. The aro10 gene of the yeast *Saccharomyces cerevisiae* or an ortholog thereof can be applied as the said gene. Phenylpyruvate Decarboxylase activity can be measured by a known method, for example, a method disclosed in the following document: Weiss, P., M., Characterization of phenylpyruvate decarboxylase, involved in auxin production of *Azospirillum brasilense*. J. Bacteriol. 189: 7626-7633 (2007).

In one or a plurality of embodiments, the ipdC gene of *Enterobacter cloacae* includes a gene that encodes an enzyme having phenylpyruvate decarboxylase activity and that is (a) the gene that has the base sequence of SEQ ID NO: 1, (b) a gene that has the base sequence of SEQ ID NO: 1 in which one or a plurality of bases are deleted, substituted, or added, and thereby has 45% or more of identity with the base sequence of SEQ ID NO: 1, or (c) a gene that hybridizes, under stringent conditions, to a gene having a base sequence complementary to the gene that has the base sequence of SEQ ID NO: 1.

In one or a plurality of embodiments, the identity is 50% or more, 60% or more, 70% or more, 80% or more, 90% or more, 95% or more, 97% or more, or alternatively, 98% or more.

The above-mentioned "stringent conditions" refer to common conditions, for example, the conditions described in Molecular Cloning, A Laboratory Manual, Second Edition, 1989, Vol 2, p 11.45. More specifically, the "stringent conditions" refer to conditions in a case where hybridization occurs at a temperature 5 or 10° C. lower than a melting temperature (Tm) of a complete hybrid.

Activation of Shikimate Pathway

In addition, in the coryneform bacterium as a host, a shikimate pathway is preferably activated, with a view to improving the production of 2-phenylethanol. The activation of the shikimate pathway in the present disclosure, in one or a plurality of embodiments, is the enhancement of the shikimate pathway, and in one or a plurality of other embodiments, the activation of the shikimate pathway encompasses the heterologous expression and/or the promotion of the expression caused by the introduction of a gene relating to the shikimate pathway.

In the present disclosure, the activation of the shikimate pathway in one or a plurality of embodiments includes introducing, into the coryneform bacterium as a host, at least one gene selected from the group consisting of: a gene that encodes an enzyme having 3-deoxy-D-arabino-heptulosonate-7-phosphate (DAHP) synthase activity; a gene that encodes an enzyme having at least either chorismate mutase activity or prephenate dehydrogenase activity; and a gene that encodes an enzyme having shikimate kinase activity.

In the present disclosure the gene relating to the shikimate pathway does not have to be limited to those described above, and another gene relating to the shikimate pathway may be introduced.

3-Deoxy-D-Arabino-Heptulosonate-7-Phosphate (DAHP) Synthase

The DAHP synthase is an enzyme that catalyzes a reaction that produces DAHP from phosphoenolpyruvate (PEP) and erythrose-4-phosphate (E4P). The gene that encodes an enzyme having DAHP synthase activity is not limited particularly, and may be derived from any of microorganisms, plants including roses, or animals. Examples of the same include DAHP synthase aroF, aroG, and aroH, as well as orthologs of the same. From the viewpoint of the productivity of 2-phenylethanol, the gene is preferably a feedback inhibition resistant mutant-type aroG gene or an ortholog of the same, or more preferably a feedback inhibition resistant mutant-type aroG gene derived from bacteria of the genus *Escherichia* such as *Escherichia coli* or an ortholog of the same.

The DAHP synthase activity can be measured by a known method, for example, a method disclosed in the following document: Liu Y J, Li P P, Zhao K X, Wang B J, Jiang C Y, Drake H L, Liu S J. *Corynebacterium glutamicum* contains 3-deoxy-D-arabino-heptulosonate 7-phosphate synthases that display novel biochemical features. Appl Environ Microbiol. 74: 5497-503(2008).

Chorismate Mutase/Prephenate Dehydrogenase

Chorismate mutase (EC 5.4.99.5)/prephenate dehydrogenase (EC 4.2.1.51) are bifunctional enzymes that catalyze a reaction that produces phenylpyruvate from chorismate. The gene that encodes an enzyme having chorismate mutase/prephenate dehydrogenase activity is not limited particularly, and may be derived from any of microorganisms, plants including roses, or animals. From the viewpoint of the productivity of 2-phenylethanol, the gene is preferably a feedback inhibition resistant mutant-type pheA gene, or more preferably a gene derived from bacteria of the genus *Escherichia* such as *Escherichia coli*.

Each of the genes of chorismate mutase and prephenate dehydrogenase can be applied alone, and each of the same is preferably of a feedback inhibition resistant mutant type.

The chorismate mutase activity and the prephenate dehydrogenase can be measured by a known method, for example, a method disclosed in the following document: Zhou H, Liao X, Wang T, Du G, Chen J. Enhanced 1-phenylalanine biosynthesis by co-expression of pheA (fbr) and aroF (wt). Bioresour Technol. 101: 4151-4156(2010).

Shikimate Kinase

Shikimate kinase (EC 2.7.1.71) is an enzyme that catalyzes a reaction of producing shikimate-3-phosphate from shikimate.

The gene that encodes this enzyme is not limited particularly, and may be derived from any of microorganisms, plants including roses, or animals. From the viewpoint of the productivity of 2-phenylethanol, the gene is preferably an aroL (shikimate kinase) gene, more preferably an aroL gene of bacteria of the genus *Escherichia* such as *Escherichia coli* or an ortholog of the same, or further preferably an aroL gene of *Escherichia coli* or an ortholog of the same. The gene may be an aroK (shikimate kinase) gene derived from *Escherichia coli*, an aroK gene derived from *Corynebacterium glutamicum*, or an ortholog of the same. The shikimate kinase activity can be measured by a known method, for example, a method disclosed in the following document: R C DeFeyter, Purification and properties of shikimate kinase II from *Escherichia coli* K-12, J. Bacteriol. 165: 331-333 (1986).

Alcohol Dehydrogenase Gene

In the coryneform bacterium transformant according to the present disclosure, an alcohol dehydrogenase gene may be further introduced, with a view to improving the production of 2-phenylethanol.

Alcohol dehydrogenase (EC1.1.1.1) is an enzyme that catalyzes a reaction of producing alcohol from aldehyde. Herein it is an enzyme that catalyzes a reaction for producing 2-phenylethanol from phenylacetaldehyde. The enzyme may be an enzyme other than alcohol dehydrogenase, as long as it can enable the production of 2-phenylethanol from phenylacetaldehyde, and the enzyme is, for example, any of phenylacetaldehyde reductase (EC1.1.1.-), aryl alcohol dehydrogenase (or referred to also as benzyl alcohol dehydrogenase) (EC1.1.1.90), aldehyde dehydrogenase, and phenylethanol dehydrogenase.

The gene of this enzyme is not limited particularly, and may be derived from any of microorganisms, plants including roses, or animals. From the viewpoint of the productivity of 2-phenylethanol, the gene is preferably a yjgB (alcohol dehydrogenase) gene, more preferably a yjgB gene of bacteria of the genus *Escherichia* or an ortholog of the same, or further preferably a yjgB gene of *Escherichia coli* or an ortholog of the same.

The enzyme may be yqhD (alcohol dehydrogenase) or yahK (aldehyde reductase) derived from *Escherichia coli*. Apart from these, the enzyme may be adhC (alcohol dehydrogenase) similar to aryl alcohol dehydrogenase derived from *Lactobacillus brevis*, adh1 or adh2 as alcohol dehydrogenase derived from *Saccharomyces cerevisiae*, or an ortholog of the same.

The alcohol dehydrogenase activity can be measured by a known method, for example, a method disclosed in the following document: Retno Indrati, Purification and properties of alcohol dehydrogenase from a mutant strain of *Candida guilliermondii* deficient in one form of the enzyme Can. J. Microbiol., 38: 953-957(1992).

(II) Method for Producing 2-Phenylethanol

By causing a reaction of the above-described transformant according to the present disclosure in a reaction solution containing a carbon source, 2-phenylethanol can be produced. The present disclosure, in one aspect, relates to a 2-phenylethanol producing method that includes causing the transformant according to the present disclosure to react in water containing a saccharide.

Growth of Microorganism

Before the reaction, the transformant is preferably cultured and grown under aerobic conditions at a temperature of about 25° C. to 38° C. for about 12 to 48 hours.

Culture Medium The culture medium used for aerobic culture of the transformant before the reaction may be a natural medium or a synthetic medium containing a carbon source, a nitrogen source, inorganic salts, other nutritional substances, etc.

Examples of the carbon source that can be used include saccharides (monosaccharides such as glucose, fructose, mannose, xylose, arabinose, and galactose; disaccharides such as sucrose, maltose, lactose, cellobiose, xylobiose, and trehalose; polysaccharides such as starch; and molasses); saccharide alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin. These carbon sources may be used alone or as a mixture of two or more thereof.

The nitrogen source that can be used is, for example, an inorganic or organic ammonium compound, such as ammonium chloride, ammonium sulfate, ammonium nitrate, or ammonium acetate; urea; aqueous ammonia; sodium nitrate; or potassium nitrate. Nitrogen-containing organic compounds, such as corn steep liquor, meat extract, peptone, NZ-amine, protein hydrolyzate, amino acid, etc. may also be used. These nitrogen sources may be used alone or as a mixture of two or more thereof. The concentration of these nitrogen sources in the culture medium may be about 0.1 to 10 w/v % usually, though it varies depending on the kind of the nitrogen compound used.

The inorganic salt is, for example, potassium dihydogen phosphate, dipotassium hydrogen phosphate, magnesium sulfate, sodium chloride, iron (II) nitrate, manganese sulfate, zinc sulfate, cobalt sulfate, or calcium carbonate. Only one kind of these inorganic salts or a mixture of two or more finds may be used. The concentration of the inorganic salts in the culture medium may be about 0.01 to 1 w/v % usually, though it varies depending on the kind of the inorganic salts used.

Examples of the nutritional substances include meat extract, peptone, polypeptone, yeast extract, dry yeast, corn steep liquor, skim milk powder, defatted soybean hydrochloric acid hydrolyzate, and extract from animals, plants or microorganisms, and degradation products thereof. The concentration of the nutritional substances in the culture medium may be about 0.1 to 10 w/v % usually, though it varies depending on the kind of the nutritional substances used.

Further, vitamins may be added as required. Examples of the vitamins include biotin, thiamin (vitamin B1), pyridoxine (vitamin B6), pantothenic acid, inositol, nicotinic acid, etc. The pH of the culture medium is preferably about 6 to 8.

Specific examples of the preferable culture medium for *Corynebacterium glutamicum* include A-medium [Inui, M. et al., Metabolic analysis of *Corynebacterium glutamicum* during lactate and succinate productions under oxygen deprivation conditions. J. Mol. Microbiol. Biotechnol. 7: 182-196 (2004)], and BT-medium [Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8: 91-103 (2004)], etc. These culture media may be prepared so as to contain a saccharide at a concentration in the above-mentioned range when used.

The reaction solution that can be used is water, buffer solution or inorganic salt medium containing a saccharide.

Examples of the buffer solution include phosphate buffer, Tris-buffer, and carbonate buffer. The concentration of the buffer solution is preferably about 10 to 150 mM.

It is desired that biotin as a growth factor is not contained in the reaction solution, so that the transformant should not grow substantially.

The inorganic salt medium is a medium containing one, two, or more kinds of the following inorganic salts: potassium dihydrogen phosphate, dipotassium hydrogen phosphate, magnesium sulfate, sodium chloride, iron (II) nitrate, manganese sulfate, zinc sulfate, cobalt sulfate, and calcium carbonate. Among these, a medium containing magnesium sulfate is preferable. A specific example of the inorganic salt medium is a BT-medium disclosed in Omumasaba, C. A. et al, *Corynebacterium glutamicum* glyceraldehyde-3-phosphate dehydrogenase isoforms with opposite, ATP-dependent regulation. J. Mol. Microbiol. Biotechnol. 8: 91-103 (2004). The concentration of the inorganic salts in the culture medium may be about 0.01 to 1 w/v % usually, though it varies depending on the kind of the inorganic salt used.

The pH of the reaction solution is preferably about 6 to 8. During the reaction, preferably the pH of the reaction solution is controlled at around neutrality, particularly about 7, with use of an aqueous solution of ammonium or sodium hydroxide aqueous solution, by using a pH controller (for example, DT-1023 model manufactured by ABLE Corporation).

Reaction Conditions

The reaction temperature, that is, the temperature for keeping the transformant alive during the reaction is preferably about 20° C. to 50° C., and more preferably about 25° C. to 47° C. When the temperature is in the above-described range, 2-phenylethanol can be efficiently produced.

The reaction period is preferably about 1 to 7 days, and more preferably about 1 to 3 days. The culture may be a batch process, a fed-batch process, or a continuous process. Among them, a batch process is preferred.

Aeration Conditions

The reaction may be performed under reducing conditions, or slightly aerobic conditions. Under any conditions, the reaction is caused under conditions where substantially no growth of *Corynebacterium glutamicum* occurs, and therefore 2-phenylethanol can be produced more efficiently.

The reducing conditions are defined based on the oxidation-reduction potential of the reaction solution. The oxidation-reduction potential of the reaction solution is preferably about −200 mV to about −500 mV, and more preferably about −250 mV to −500 mV.

The reduction state of the reaction solution can be simply estimated using a resazurin indicator (in reducing conditions, decolorization from blue to colorless is observed). However, for precise measurement, a redox-potential meter (for example, ORP Electrodes made by BROADLEY JAMES) is used.

As a method of preparing a reaction solution under reducing conditions, any publicly known method can be used without limitation.

For example, as a liquid medium for preparation of the reaction solution, an aqueous solution for a reaction solution may be used instead of distilled water or the like. As reference for preparation of the aqueous solution for a reaction solution, for example, the method for preparing a culture solution for strictly anaerobic microorganisms, such as sulfate-reducing microorganisms (Pfennig, N. et al. (1981): The dissimilatory sulfate-reducing bacteria, In The Prokaryotes, A Handbook on Habitats, Isolation and Identification of Bacteria Ed. By Starr, M. P. et al., p. 926-940, Berlin, Springer Verlag.), and "Nogeikagaku Jikkensho" Ed. by Kyoto Daigaku Hogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction solution under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes, whereby an aqueous solution for a reaction solution under reducing conditions can be obtained.

Further, by adding a suitable reducing agent (for example, thioglycolic acid, ascorbic acid, cysteine hydrochloride, mercaptoacetic acid, thiol acetic acid, glutathione, or sodium sulfide), an aqueous solution for a reaction solution under reducing conditions can be prepared.

These methods may be suitably combined, too, to prepare an effective aqueous solution for a reaction solution under reducing conditions.

In a case where reducing conditions during the reaction are maintained, it is desirable that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. For allowing the metabolic functions in the cells of the coryneform bacterium transformant of the present disclosure to work efficiently during the reaction, addition of a solution of various nutrients or a reagent solution for adjusting and maintaining the pH of the reaction system may be needed in some cases. In such a case, for more effective prevention of oxygen incorporation, it is effective to remove oxygen in the solutions to be added, in advance.

In a case where slightly aerobic conditions are maintained in the middle of the reaction, the reaction can be caused under conditions of an aeration amount at a low level such as 0.5 vvm or less, and an agitation speed at a low level such as 500 rpm or less. In some cases, after the start of the reaction, the aeration may be blocked at an appropriate time, and the reaction may be allowed under an agitation speed of 100 rpm or less, combined with a state of an enhanced aerophobicity.

Collection of 2-Phenylethanol

Through the culture performed in the above-described manner, 2-phenylethanol is produced in the reaction solution. By collecting the reaction solution, 2-phenylethanol can be collected, and further, 2-phenylethanol can also be separated from the reaction solution by a known method. Examples of such a known method include the distillation method, the membrane permeation method, the resin adsorption method, and the organic solvent extraction method.

The present disclosure relates to the following, in one or a plurality of embodiments:

<1> A coryneform bacterium transformant in which a shikimate pathway is activated, wherein a gene that encodes an enzyme having phenylpyruvate decarboxylase activity is further introduced in the coryneform bacterium transformant in such a manner that the gene can be expressed.

<2> The coryneform bacterium transformant according to <1>, wherein the gene that encodes an enzyme having phenylpyruvate decarboxylase activity is an ipdC gene of *Enterobacter cloacae*.

<3> The coryneform bacterium transformant according to <1> or <2>, wherein the gene that encodes an enzyme having phenylpyruvate decarboxylase activity includes any of (a) the gene that has the base sequence of SEQ ID NO: 1, (b) a gene that has the base sequence of SEQ ID NO: 1 in which one or a plurality of bases are deleted, substituted, or added and thereby has 45% or more of identity with the base sequence of SEQ ID NO: 1, or (c) a gene that hybridizes, under stringent conditions, to a gene having a base sequence complementary to the gene that has the base sequence of SEQ ID NO: 1.

<4> The coryneform bacterium transformant according to any one of <1> to <3>, wherein the activation of the shikimate pathway includes introducing, into a coryneform bacterium as a host, at least one gene selected from the group consisting of: a gene that encodes an enzyme having 3-deoxy-D-arabino-heptulosonate-7-phosphate (DAHP) synthase activity; a gene that encodes an enzyme having at least either chorismate mutase activity or prephenate dehydrogenase activity; and a gene that encodes an enzyme having shikimate kinase activity.

<5> The coryneform bacterium transformant according to <4>, wherein the gene that encodes an enzyme having 3-deoxy-D-arabino-heptulosonate-7-phosphate (DAHP) synthase activity, and the gene that encodes an enzyme having at least either chorismate mutase activity or prephenate dehydrogenase activity, are a gene that encodes the enzyme having feedback inhibition resistant.

<6> The coryneform bacterium transformant according to <4> or <5>, wherein the gene that encodes an enzyme having 3-deoxy-D-arabino-heptulosonate-7-phosphate (DAHP) synthase activity, the gene that encodes an enzyme having at least either chorismate mutase activity or prephenate dehydrogenase activity, and the gene that encodes an enzyme having shikimate kinase activity are a gene of *Escherichia coli*.

<7> The coryneform bacterium transformant according to any one of <1> to <6>, wherein at least one selected from the group consisting of a lactate dehydrogenase gene, a 3-dehydroshikimate dehydratase gene, a dihydroxyacetone phosphatase gene, and a phenylalanine uptake transporter gene is disrupted.

<8> The coryneform bacterium transformant according to any one of <1> to <7>, wherein a coryneform bacterium as a host is *Corynebacterium glutamicum*.

<9> The coryneform bacterium transformant according to any one of <1> to <8>, wherein a coryneform bacterium as a host is *Corynebacterium glutamicum* R (FERM BP-18976), ATCC13032, or ATCC13869 (DSM1412).

<10> A coryneform bacterium transformant of *Corynebacterium glutamicum* strain 2PE97 (Accession Number: NITE BP-02830).

<11> A 2-phenylethanol producing method including causing the coryneform bacterium transformant according to any one of <1> to <10> to react in water containing a saccharide.

<12> The 2-phenylethanol producing method according to <11>, wherein the saccharide is selected from the group consisting of glucose, fructose, mannose, xylose, arabinose, galactose, sucrose, maltose, lactose, cellobiose, xylobiose, trehalose, and mannitol.

EXAMPLE

The following description describes the present disclosure in detail, while referring to examples, but the present disclosure is not limited to these examples.

Example 1

Construction of 2-Phenylethanol Producing Strain (1) Preparation/Obtainment of Chromosomal DNA The following were cultured according to information obtained from organizations from which the strains are available. *Corynebacterium glutamicum* R (FERM BP-18976); *Azospirillum brasilense* NBRC 102289; *Beijerinckia indica* subsp. indica DSM1715; *Bifidobacterium animalis* subsp. *lactis* JCM 10602; *Bradyrhizobium diazoefficiens* JCM 10833; *Bradyrhizobium elkanii* JCM 10832; *Bradyrhizobium japonicum* JCM 20679; *Bradyrhizobium lablabi* NBRC 108826; *Burkholderia multivorans* NBRC 102086; *Caldilinea aerophila* DSM 14535; *Chromohalobacter salexigens* ATCC BAA-138; *Comamonas testosteroni* NBRC 14951; *Corynebacterium aurimucosum* JCM 11766; *Corynebacterium kroppenstedtii* JCM 11950; *Debaryomyces hansenii* JCM 1990; *Delftia acidovorans* JCM 5833; *Desulfovibrio magneticus* DSM 13731; *Enterobacter cloacae* NBRC 13535; *Enterobacter hormaechei* ATCC 49162; *Erwinia herbicola* NBRC 102470; *Escherichia coli* K-12 MG1655; *Kluyveromyces lactis* JCM 22014; *Komagataella phaffii* ATCC 20864; *Lachancea thermotolerans* JCM 19085; *Lactococcus lactis* NBRC 100933; *Mycobacterium smegmatis* MC(2) 155 ATCC 700084; *Nostoc* sp. PCC 73102 ATCC29133; *Pandoraea vervacti* NBRC 106088; *Polaromonas naphthalenivorans* ATCC BAA-779; *Providencia rustigianii* JCM 3953; *Providencia stuartii* ATCC 25827; *Pseudomonas putida* NBRC 14164; *Ralstonia eutropha* IAM 12368; *Rhodococcus jostii* JCM 11615; *Rhodopseudomonas palustris* ATCC BAA-98; *Rhodospirillum rubrum* ATCC 11170; *Saccharomyces cerevisiae* NBRC 2376; *Saccharopolyspora erythraea* JCM 4748; *Staphylococcus epidermidis* NBRC 12993; *Staphylococcus haemolyticus* JCSC 1435; *Staphylococcus saprophyticus* ATCC 15305; and *Streptomyceslividans* NBRC 15675. Thereafter, chromosomal DNA of these was prepared by using DNA genome extraction kits (trade name: illustra bacteria genomicPrep Mini Spin Kit, available from GE Healthcare Japan Corporation). The pdc genes of *Prunus persica* and Rosa hybrid cultivarwere obtained by GeneArt artificial gene synthesis (Thermo Fisher Scientific K.K.).

(2) Construction of Plasmid for Expression of 2-phenylethanol-Production-Related Gene Primer sequences used for isolating target enzyme genes are shown in Table 1. In PCR, Veriti Thermal Cycler (Thermo Fisher Scientific K.K.) was used, and PrimeSTAR HS DNA Polymerase (Takara Bio Inc.) was used as a reaction reagent.

DNA fragments obtained were introduced into cloning vectors containing PgapA promoters (pCRB207 [Appl Environ Microbiol. 78(3): 865-875 (2012)], pCRB209 [WO2012/033112], pCRB210 [WO2012/033112]). The mutation introduction into the pheA gene was carried out by linking a PCR fragment amplified with use of a phosphorylation primer. The names of the cloning vectors introduced and the plasmids obtained are shown in Table 2.

TABLE 1

Primer for Isolation of 2-phenylethanol-Production-Related Gene

| Gene Source | Enzyme Gene | Forward | Reverse | Gene |
|---|---|---|---|---|
| *Azospirillum brasilense* | pdc | SEQ ID NO: 9 | SEQ ID NO: 10 | SEQ ID NO: 1 |
| *Corynebacterium aurimucosum* | pdc | SEQ ID NO: 11 | SEQ ID NO: 12 | SEQ ID NO: 2 |
| *Enterobacter cloacae* | pdc | SEQ ID NO: 13 | SEQ ID NO: 14 | SEQ ID NO: 3 |
| *Rhodopseudomonas palustris* | pdc1 | SEQ ID NO: 15 | SEQ ID NO: 16 | SEQ ID NO: 4 |
| *Rhodospirillum rubrum* | pdc | SEQ ID NO: 17 | SEQ ID NO: 18 | SEQ ID NO: 5 |
| *Escherichia coli* | aroL | SEQ ID NO: 19 | SEQ ID NO: 20 | SEQ ID NO: 6 |
| *Escherichia coli* | pheA | SEQ ID NO: 21 | SEQ ID NO: 22* | SEQ ID NO: 7 |
| | | SEQ ID NO: 23* | SEQ ID NO: 24 | |
| *Caldilinea aerophila* | pdc | SEQ ID NO: 25 | SEQ ID NO: 26 | SEQ ID NO: 8 |

*phosphorylation primer

TABLE 2

Plasmid for Expression of 2-phenylethanol-Production-Related Gene

| Gene Source | Enzyme Gene | Introduction Vector | Plasmid |
|---|---|---|---|
| *Azospirillum brasilense* | pdc | pCRB209 | P2pe60 |
| *Caldilinea aerophila* | pdc | pCRB209 | P2pe83 |
| *Corynebacterium aurimucosum* | pdc | pCRB209 | PGibu50 |
| *Enterobacter cloacae* | ipdC | pCRB210 | PGibu37 |
| *Rhodopseudomonas palustris* | pdc1 | pCRB209 | PGibu52 |
| *Rhodospirillum rubrum* | pdc | pCRB209 | P2pe85 |
| *Escherichia coli* | aroL | pCRB209 | Pphe223 |
| *Escherichia coli* | pheA | pCRB209 | P2pe3 |

(3) Construction of Plasmid for Chromosomal Introduction of 2-phenylethanol-Production-Related Gene A DNA region necessary for markerless introduction of a 2-phenylethanol-production-related gene into a chromosome of *Corynebacterium glutamicum* strain R was determined based on a sequence that was reported not to be essential for the growth of *Corynebacterium glutamicum* strain R [Appl. Environ. Microbiol. 71: 3369-3372 (2005)] (SSI region). This DNA region was amplified by the PCR method. The DNA fragment thus obtained was introduced into the plasmid pCRA725 for markerless gene introduction [J. Mol. Microbiol. Biotechnol. 8: 243-254(2004), JP-A-2007-295809]. Incidentally, into pCRG40, a restriction enzyme site (unique site) for incorporating a gene in the SSI region by the inverse PCR method was introduced. The primer sequences used for the isolation of the SSI regions and the inverse PCR and the obtained vectors for chromosomal introduction are shown in Table 3.

TABLE 3

Primer Sequence Used for Isolating SSI Region and Obtained Vector for Chromosomal Introduction

| Vector for Chromosomal Introduction | SSI Region | Forward | Reverse |
|---|---|---|---|
| pCRG38 | SSI8-3 | SEQ ID NO: 27 | SEQ ID NO: 28 |
| pCRG39 | SSI6-5 | SEQ ID NO: 29 | SEQ ID NO: 30 |
| pCRG40 | SSI4-5 | SEQ ID NO: 31 | SEQ ID NO: 32 |
|  |  | SEQ ID NO: 33* | SEQ ID NO: 34* |

*Primer used for Inverse PCR method

PgapA promoter fusion enzyme gene fragments were obtained from the plasmids for the expression of 2-phenylethanol-production-related genes, which were constructed as shown in Table 2, and the fragments were introduced into the plasmids for chromosomal introduction described above. Further, the plasmid pSKM8 for tkt-tal gene expression [WO2016/027870], the plasmid pCRB278 for SSI8-1 region introduction [WO2017/169399], the plasmid pCRB276 for SSIS-1 region introduction [WO2017/169399], and the plasmid pCRB259 for SSI2-2 region introduction [WO2017/146241] were also used. The plasmids for chromosomal introduction of 2-phenylethanol-production-related genes thus obtained are shown in Table 4.

TABLE 4

Plasmid for Chromosomal Introduction of 2-phenylethanol-Production-Related Gene

| Gene Source | Enzyme Gene | SSI Region | Plasmid for Chromosomal Introduction |
|---|---|---|---|
| Corynebacterium glutamicum | tkt, tal | SSI 8-1 | LKSppp27 |
| Escherichia coli | aroL | SSI8-3 | LKSphe42 |
| Escherichia coli | PheA (T304_Q306dup, A303_Q307insK) | SSI6-5 | LKS2pe2 |
|  |  | SSI2-2 | LKS2pe1 |
|  |  | SSI4-5 | LKS2pe7 |

(4) Construction of Plasmid for Chromosomal Gene Disruption of *Corynebacterium glutamicum* Strain R A DNA region necessary for markerless chromosomal gene disruption of a *Corynebacterium glutamicum* strain R was amplified by the PCR method. Each PCR fragment is linkable in overlap regions. The DNA fragment thus obtained was introduced into the plasmid pCRA725 for markerless gene disruption [J. Mol. Microbiol. Biotechnol. 8: 243-254(2004), JP-A-2007-295809]. Obtained plasmids for chromosomal gene disruption are shown in Table 5.

TABLE 5

Plasmid for Chromosomal Gene Disruption of *Corynebacterium glutamicum* Strain R

| Plasmid for Chromosomal Disruption | Disrupted Gene | Forward | Reverse |
|---|---|---|---|
| pCRG37 | cgR_2372 | SEQ ID NO: 35 | SEQ ID NO: 36* |
|  |  | SEQ ID NO: 37* | SEQ ID NO: 38 |
| pCRG41 | cgR_1237 | SEQ ID NO: 39 | SEQ ID NO: 40* |
|  |  | SEQ ID NO: 41* | SEQ ID NO: 42 |

*Primer including overlap region (5) Construction of 2-Phenylethanol Producing Strains by Chromosomal Gene Recombination The vector pCRA725 for markerless chromosomal gene introduction is a plasmid that cannot be replicated in *Corynebacterium glutamicum* R. In a case of a single crossover strain in which crossover occurs at homologous region on the chromosome introduced into the plasmid pCRA725, the strain exhibits the kanamycin resistance due to the expression of the kanamycin-resistant gene on pCRA725, and the lethality in a sucrose-containing medium due to the expression of the sacR-sacB gene of the *Bacillus subtilis*. In contrast, in a case of a double crossover strain, the strain exhibits the kanamycin sensitivity due to the loss of the kanamycin-resistant gene on pCRA725, and the growth ability in a sucrose-containing medium due to the loss of the sacR-sacB gene. A markerless chromosomal gene introduced strain, therefore, exhibits the kanamycin sensitivity and the growth ability in the sucrose-containing medium.

By the above-described methods, gene recombinant strains were constructed by using the above-described plasmids for chromosomal introduction of 2-phenylethanol-production-related genes and the above-described plasmids for chromosomal gene disruption. *Corynebacterium glutamicum* strain R, and ldhA disruption strain CRZ1 [Biotechnol Bioeng. November; 110(11): 2938-2948 (2013)] were used as host strains. Additionally, the following were also used: plasmid pCRB285 for chromosomal introduction of aroG (S180F) gene [WO2017/169399]; plasmid pCRB292 for chromosomal introduction of aroD gene [WO2017/169399]; plasmid pCRB294 for chromosomal introduction of aroE gene [WO2017/169399]; plasmid pCRB289 for chromosomal introduction of aroA gene [WO2017/169399]; plasmid pCRB287 for chromosomal introduction of aroCKB gene [WO2017/169399]; plasmid pCRB294 for chromosomal introduction of gapA gene [Appl Environ Microbiol. 78(12): 4447-4457 (2012)]; plasmid pSKM14 for chromosomal introduction of iolT1 gene [WO2016/027870]; plasmid pSKM26 for disruption of qsuB gene [WO2016/027870]; plasmid pSKM28 for disruption of hdpA gene [WO2016/027870]; and plasmid pCRC809 for disruption of ptsH gene [Microbiology. 155 (Pt11): 3652-3660 (2009)]. This chromosomal gene recombination is outlined together in Tables 6 and 7.

TABLE 6

Construction of 2-phenylethanol Producing Strains by Chromosomal Gene Recombination

| Constructed Strain | Host Strain | Recombination Plasmid |
|---|---|---|
| ES2pe1 | C. glutamicum R | pCRG37 |
| LHglc1449 | CRZ1 | pCRB285, pCRB292, pCRB294, pCRB289, pCRB287, pCRG27, pCRD906, pSKM14, LKSphe42, LKS2pe5, LKS2pe2, LKS2pe1, LKS2pe7, pSKM26, pSKM28, pCRC809, pCRG41 |

TABLE 7

Outline of 2-Phenylethanol Producing Strains
Constructed by Chromosomal Gene Recombination

| Constructed Strain | Chromosome Introduced Gene | Disrupted Chromosomal Gene |
|---|---|---|
| ES2pe1 | | cgR_2372 |
| LHglc1449 | aroG (S180F), aroD, aroE, aroA, aroCKB, tkt-tal, gapA, iolT1, aroL pheA (T304_Q306dup, A303_Q307insK) × 3 | qsuB, hdpA, ptsH, cgR_1237, ldhA |

×3: Indicating the Number of genes introduced into chromosome (6) Construction of Strain in Which Plasmid for Expression of 2-phenylethanol Producing Gene is Introduced The pdc gene, the ipdC gene, and the like were introduced into the above-described chromosomal gene recombinant strains, whereby 2-phenylethanol-producing strains were constructed. The producing strains thus constructed are outlined together in Table 8.

TABLE 8

Outline of 2-Phenylethanol Producing Strains

| Constructed Strain | Host Strain | Introduced Plasmid | Gene Source |
|---|---|---|---|
| 2PE97 | LHglc1449 | PGibu37 | *Enterobacter cloacae* |
| 2PE143 | LHglc1449 | P2pe60 | *Azospirillum brasilense* |
| 2PE144 | LHglc1449 | PGibu50 | *Corynebacterium aurimucosum* |
| 2PE145 | LHglc1449 | PGibu52 | *Rhodopseudomonas palustris* |
| 2PE146 | LHglc1449 | P2pe83 | *Caldilinea aerophila* |
| 2PE147 | LHglc1449 | P2pe85 | *Rhodospirillum rubrum* |

These strains were cultured in vitro. The strain 2PE97 as well as the strains 2PE143 to 2PE147, which produced 38 mM or more of 2-phenylethanol at 33° C. after 48 hours, were subjected to production tests by jar culture as follows.

[Test of production of 2-phenylethanol from glucose by a strain in which a gene that encodes an enzyme having phenylpyruvate decarboxylase activity was introduced]

Each of 2-phenylethanol producing gene introduced strains (strains 2PE97, 143-147) was applied to an A-agar plate [obtained by suspending the following in 1 liter of distilled water: $(NH_2)_2CO$, 2 g; $(NH_4)_2SO_4$, 7 g; $KH_2PO_4$, 0.5 g; $K_2HPO_4$, 0.5 g; $MgSO_4 \cdot 7H_2O$, 0.5 g; 0.06% (w/v) $FeSO_4 \cdot 7H_2O$+0.042% (w/v) $MnSO_4 \cdot 2H_2O$, 1 ml; 0.02% (w/v) biotin solution, 1 ml; 0.01% (w/v) thiamin solution, 2 ml; yeast extract, 2 g; vitamin assay casamino acid, 7 g; glucose, 40 g; and agar, 15 g] containing kanamycin of 50 µg/mL, and it was subjected to static culture at 33° C. for 18 hours.

One platinum loop of each of 2-phenylethanol producing gene introduced strains (strains 2PE97, 143-147), grown on the above-described plates, was inoculated in a test tube containing 10 ml of an A-liquid medium [obtained by dissolving the following in 1 liter of distilled water: $(NH_2)_2CO$, 2 g; $(NH_4)_2SO_4$, 7 g; $KH_2PO_4$, 0.5 g; $K_2HPO_4$, 0.5 g; $MgSO_4 \cdot 7H_2O$, 0.5 g; 0.06% (w/v) $FeSO_4 \cdot 7H_2O$+ 0.042% (w/v) $MnSO_4 \cdot 2H_2O$, 1 ml; 0.02% (w/v) biotin solution, 1 ml; 0.01% (w/v) thiamin solution, 2 ml; yeast extract, 2 g; vitamin assay casamino acid, 7 g; and glucose, 40 g] containing kanamycin of 50 µg/mL, and it was subjected to aerobic shaking culture at 33° C. for 18 hours.

The culture solution thus obtained was transferred to a 100 mL jar fermentor device so that an initial OD610 was 0.8, and glucose as a substrate was added (initial concentration: 100 g/L) to the A-medium. The pH of the culture reaction solution was adjusted using 2.5 N aqueous ammonia so that it would not become below 7.0, and culturing was carried out at 33° C. under aerated conditions. Glucose was appropriately added when the concentration thereof decreased.

Each culture solution sampled was centrifuged (4° C., 10,000×g, 5 minutes), and the product was analyzed by using the supernatant obtained. The glucose concentration in the culture solution was measured by using a glucose sensor (OSI BF-5D). The concentration of 2-phenylethanol was measured with a HPLC system manufactured by Shimadzu Corporation, in which a COSMOSIL C18-AR-II of Nacalai Tesque was used as a separation column. The separation conditions of HPLC were as follows: 40% methanol and 0.069% perchloric acid were used in the mobile phase, the flow rate was set to 1.0 ml/min, and the column temperature was set to 40° C.

As described above, the gene that encodes an enzyme having phenylpyruvate decarboxylase activity was cloned, and was introduced into the strain LHglc1449 as a coryneform bacterium host for 2-phenylethanol production, for examination. Table 9 shows recombinant strains that exhibited productivities of 2-phenylethanol concentrations of 25 mM or more after 48-hour culture with the host, the culture, and the reaction conditions described above. The strain 2PE97 produced the highest concentration 2-Phenylethanol.

TABLE 9

Comparison of concentrations of 2-phenylethanol
produced by producing strains in
which enzyme genes having Pdc
activities were introduced

| Recombinant Strain | Concentration of 2-phenylethanol (mM) |
|---|---|
| 2PE97 | 55.6 |
| 2PE143 | 47.7 |
| 2PE144 | 48.9 |
| 2PE145 | 48.2 |
| 2PE146 | 39.6 |
| 2PE147 | 26.1 |

*Corynebacterium glutamicum* strain 2PE97 was deposited in Incorporated Administrative Agency National Institute of Technology and Evaluation, NITE Patent Microorganisms Depositary (NPMD) (2-5-8-122 Kazusakamatari, Kisarazu-shi, Chiba 292-0818 Japan) as an international depositary authority, under Accession Number NITE BP-02830 on Nov. 22, 2018.

Example 2

Experiment of 2-Phenylethanol Production of *Corynebacterium glutamicum* Strain in which a 2-Phenylethanol Producing Gene was Introduced

*Corynebacterium glutamicum* strain in which 2-phenylethanol producing gene was introduced (strain 2PE97) was applied to an A-agar plate (the same as that described above) containing kanamycin of 50 µg/m L, and was subjected to static culture at 33° C. for 18 hours.

One platinum loop of the strain 2PE97, grown on the above-described plates, was inoculated in a test tube containing 10 ml of the A-liquid medium (the same as that described above) containing kanamycin of 50 µg/m L, and was subjected to aerobic shaking culture at 33° C. for 18 hours.

The culture solution thus obtained was transferred to a 100 mL jar fermentor device so that an initial OD610 was 0.8, glucose as a substrate was added (initial concentration: 100 g/L) to the A-medium. The pH of the culture solution was adjusted using 2.5 N aqueous ammonia so that it would not become below 7.0, and culturing was carried out at 33° C. under aerated conditions. Glucose was appropriately added when the concentration thereof decreased.

Each culture solution sampled was centrifuged (4° C., 10,000×g, 5 minutes), and the product was analyzed by using the supernatant obtained. The glucose concentration in the culture solution was measured by using a glucose sensor (OSI BF-5D). The concentration of 2-phenylethanol was measured with a HPLC system manufactured by Shimadzu Corporation, in which a COSMOSIL C18-AR-II of Nacalai Tesque was used as a separation column. The separation conditions of HPLC were as follows: 40% methanol and 0.069% perchloric acid were used in the mobile phase, the flow rate was set to 1.0 ml/min, and the column temperature was set to 40° C. As a result of 48-hour reaction, the yield of 2-phenylethanol was 6.5 g/L (FIG. 1). On the other hand, a gene recombinant in which the phenylpyruvate decarboxylase gene was not introduced, used as a control, did not produce 2-phenylethanol at all.

The strain 2PE97 produced in Example 1 was applied to an A-agar plate (the same as that described above) containing kanamycin of 50 µg/mL, and was left to stand at 33° C. for 16 hours.

One platinum loop of the strain 2PE97, grown on the above-described plates, was inoculated in a test tube containing 10 ml of the A-liquid medium (the same as that described above) containing kanamycin of 50 µg/mL, and was subjected to aerobic shaking culture at 33° C. for 16 hours.

The strain 2PE97, grown under the above-described conditions, was inoculated in a 2-liter Erlenmeyer flask containing 500 ml of the A-liquid medium (the same as that described above) containing kanamycin of 50 µg/mL, and was subjected to aerobic shaking culture at 33° C. for 16 hours.

Bacterial cells thus cultured and grown were collected by centrifugation (4° C., 5,000×g, 10 minutes). The bacterial cells thus obtained were suspended in 400 ml of BT(-urea)-liquid medium [0.7% $(NH_4)_2SO_4$, 0.05% $KH_2PO_4$, 0.05% $K2HPO_4$, 0.05% $MgSO_4·7H_2O$, 0.06% (w/v) $FeSO_4·7H_2O$+ 0.000042% (w/v) $MnSO_4·2H_2O$, 0.00002% (w/v) thiamin solution] so as to have a final bacteria cell concentration of 5%. The culture solution thus obtained was transferred to a 1-liter jar fermentor device, glucose as a substrate was added (initial concentration: 100 g/L), and the reaction was allowed to occur at 33° C., with the pH of the reaction solution being adjusted using 5.0 N aqueous ammonia so that it would not become below 7.0, in a state where bacterial cells did not grow, under conditions of the aeration amount of 1.0 vvm as well as an agitation speed of 900 rpm. A synthetic adsorption resin XAD2 (Organo Corporation) was added so as to have a final concentration of 5% (w/v) for the purpose of causing the resin to adsorb 2-phenylethanol.

Each reaction solution sampled was centrifuged (4° C., 10,000×g, 5 minutes), and the product was analyzed by using the supernatant obtained. The glucose concentration in the culture solution was measured by using a glucose sensor (OSI BF-5D). The concentration of 2-phenylethanol was measured with a HPLC system manufactured by Shimadzu Corporation, in which a COSMOSIL C18-AR-II of Nacalai Tesque was used as a separation column. The separation conditions of HPLC were as follows: 40% methanol and 0.069% perchloric acid were used in the mobile phase, the flow rate was set to 1.0 ml/min, and the column temperature was set to 40° C. The 2-phenylethanol that the XAD2 adsorbed was eluted by acetone, and thereafter it was similarly subjected to the HPLC analysis.

Figure 2:
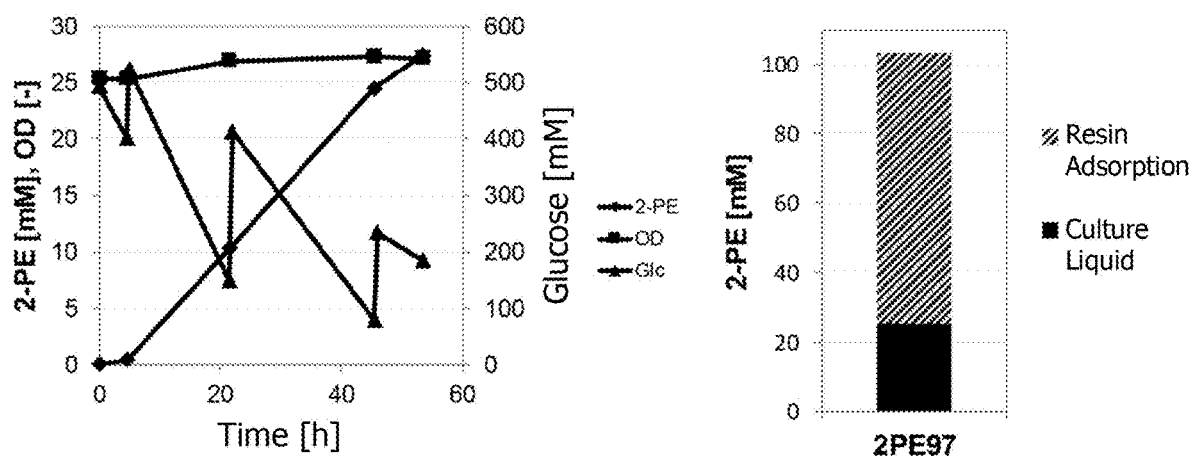
FIG. 2 shows the production of 2-phenylethanol by resin adsorption under aerobic reaction conditions.

As a result of the production reaction in which the transformant substantially did not grow, accumulation of 2-phenylethanol was observed (FIG. 2, the left part, illustrates changes with time of the concentration of 2-phenylethanol remaining in the culture solution). A total of 12.8 g/L (105 mM) of 2-phenylethanol, including that adsorbed to the resin, was produced during 53.5 hours of the reaction. The details of the same are: 78 mM adsorbed to the resin; and 27 mM remaining in the culture solution (FIG. 2, the right part).

Example 3

Tests Regarding Suitability as Host for 2-Phenylethanol Production

Influence of 2-Phenylethanol to Aerobic Growth

Tests regarding growth inhibition by 2-phenylethanol in aerobic culture were carried out on *Corynebacterium glutamicum, Escherichia coli, Pseudomonas putida*, and *Kluyveromyces marxianus*.

*Corynebacterium glutamicum* R was applied to an A-agar plate (the same as that described above), and was left to stand in a dark place at 33° C. for 15 hours.

One platinum loop of *Corynebacterium glutamicum* R grown on the plate described above was inoculated in a test tube having therein 10 ml of the A-liquid medium, and aerobic shaking culture was carried out at 33° C. for 13 hours.

*Corynebacterium glutamicum* R grown under the above-described conditions was inoculated in 100 ml of the A-liquid medium (the same as that described above) so that the initial bacterial cell concentration OD610=0.05 was achieved. Simultaneously, 2-phenylethanol was added so that the final concentrations thereof became 0, 10, 20, 30, 40, and 50 mM, and aerobic shaking culture was carried out at 33° C. The growth of bacterial cells was determined by measuring the absorbance of OD610.

*Escherichia coli* MG1655 was applied to an LB-agar plate [containing 1% polypeptone, 0.5% yeast extract, 0.5% sodium chloride, and 1.5% agar], and was left to stand at 37° C. for 15 hours in a dark place.

One platinum loop of *Escherichia coli* MG1655 grown on the plate described above was inoculated in a test tube having therein 10 ml of an LB-liquid medium [containing 1% polypeptone, 0.5% yeast extract, and 0.5% sodium chloride], and was subjected to aerobic shaking culture at 37° C. for 13 hours.

*Escherichia coli* MG1655 grown under the above-described conditions was inoculated in 100 ml of the LB-liquid medium so that the initial bacterial cell concentration OD610=0.05 was achieved. Simultaneously, 2-phenylethanol was added so that the final concentrations thereof became 0, 10, 20, 30, 40, and 50 mM, and aerobic shaking culture was carried out at 33° C. The growth of bacterial cells was determined by measuring the absorbance of OD610.

*Pseudomonas putida* S12 was applied to an LB-agar plate [containing 1% polypeptone, 0.5% yeast extract, 0.5% sodium chloride, and 1.5% agar], and was left to stand at 30° C. for 15 hours in a dark place.

One platinum loop of *Pseudomonas putida* S12 grown on the plate described above was inoculated in a test tube having therein 10 ml of an LB(+glucose)-liquid medium [containing 1% polypeptone, 0.5% yeast extract, 0.5% sodium chloride, and 0.4% glucose], and was subjected to aerobic shaking culture at 33° C. for 13 hours. The *Pseudomonas putida* S12 strain grown under the above-described conditions was inoculated in 100 ml of the LB(+glucose)-liquid medium so that the initial bacterial cell concentration OD610=0.05 was achieved. Simultaneously, 2-phenylethanol was added so that the final concentrations thereof became 0, 10, 20, 30, 40, and 50 mM, and aerobic shaking culture was carried out at 30° C. The growth of bacterial cells was determined by measuring the absorbance of OD610.

Further, *Kluyveromyces marxianus* was applied to a YPD-agar plate [containing 2% polypeptone, 1% yeast extract, 2% glucose, and 1.5% agar], and was left to stand at 30° C. for 15 hours in a dark place.

One platinum loop of *Kluyveromyces marxianus* grown on the plate described above was inoculated in a test tube having therein 10 ml of a YPD-liquid medium [containing 2% polypeptone, 1% yeast extract, and 2% glucose], and was subjected to aerobic shaking culture at 40° C. for 13 hours.

*Kluyveromyces marxianus* grown under the above-described conditions was inoculated in 100 ml of the YPD-liquid medium so that the initial bacterial cell concentration OD610=0.05 was achieved. Simultaneously, 2-phenylethanol was added so that the final concentrations thereof became 0, 10, 20, 30, 40, and 50 mM, and aerobic shaking culture was carried out at 40° C. The growth of bacterial cells was determined by measuring the absorbance of OD610.

Figure 3:
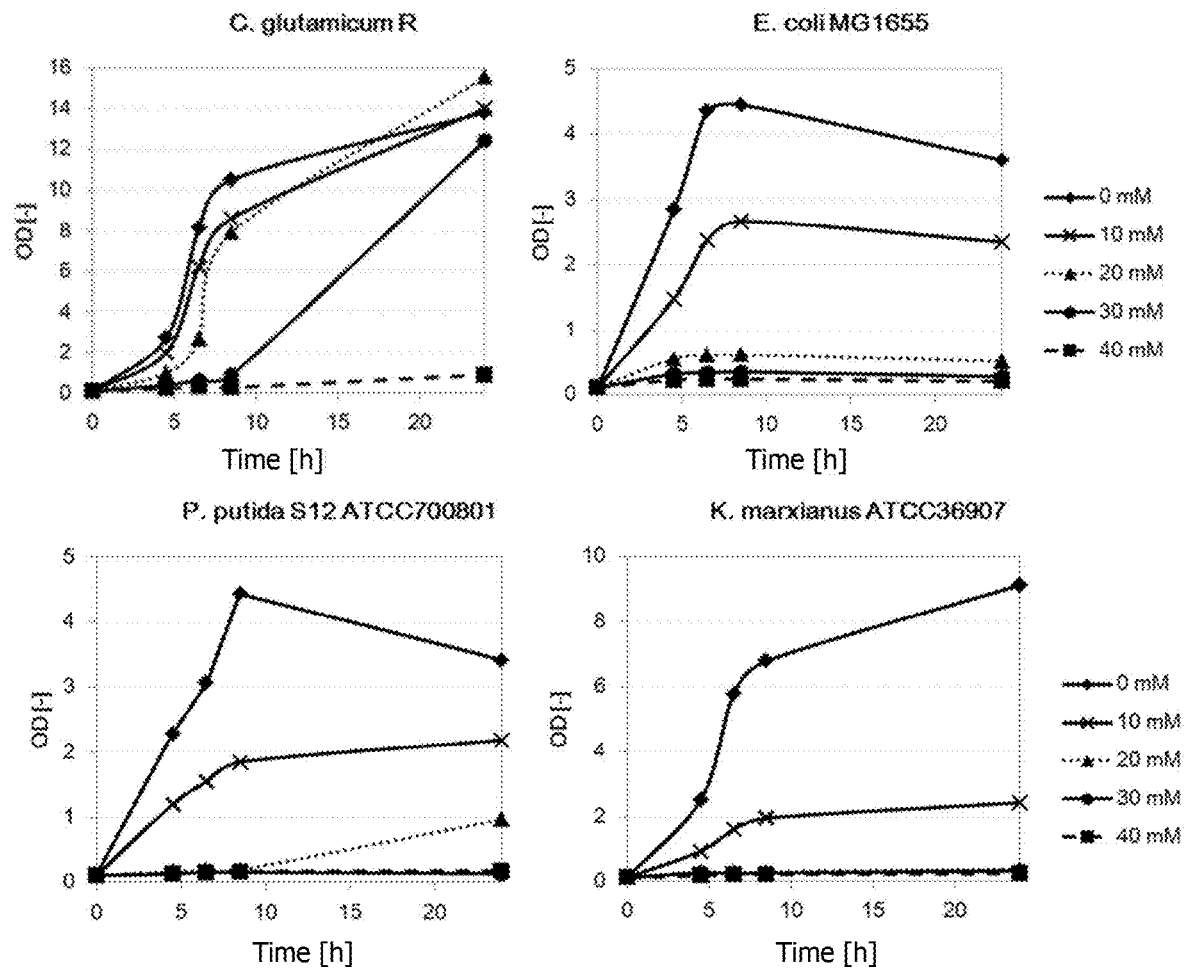
FIG. 3 shows tests for determining suitability as a host for 2-phenylethanol production.

How the addition of 2-phenylethanol to the media influenced aerobic growth was analyzed, and the results are shown in FIG. 3. The growth of *Escherichia coli* was significantly inhibited under the presence of 20 mM 2-phenylethanol, and the growth thereof was substantially completely inhibited under the presence of 30 mM 2-phenylethanol.

*Pseudomonas putida* S12, reported to be a solvent-resistant bacterium, exhibited similar tendencies, and the growth thereof was completely inhibited under the presence of 30 mM 2-phenylethanol.

In contrast, the growth of *Corynebacterium glutamicum* was not influenced at all under the presence of 20 mM 2-phenylethanol that strongly inhibited the growth of *Escherichia coli*, *Pseudomonas putida*, and *Kluyveromyces marxianus*. In addition, under the presence of 30 mM 2-phenylethanol that substantially completely inhibited the growth of *Escherichia coli*, *Pseudomonas putida*, and *Kluyveromyces marxianus*, the growth of *Corynebacterium glutamicum* was delayed, but was improved 24 hours after.

The above-described results show that *Corynebacterium glutamicum* exhibited a high resistance against 2-phenylethanol, as compared with *Escherichia coli*, *Pseudomonas putida*, and *Kluyveromyces marxianus*. Thus, it was proved that *Corynebacterium glutamicum* is highly suitable as a host for 2-phenylethanol production.

INDUSTRIAL APPLICABILITY

According to the present disclosure, it is possible to produce 2-phenylethanol from a saccharide raw material with a practical efficiency.

|  |  | PCT |
|---|---|---|
| 0-1 | Form PCT/RO/134 | JPO-PAS |
| 0-1-1 | This description of a deposited microorganism or another biological specimen (PCT Rule 13(2)) is made by the system described at right. | i370 |
| 0-2 | International Application Number | |
| 0-3 | Applicant or Attorney Number | H4698-01 |
| 1 | The description below relates to the microorganism or biological specimen described in the detailed description of the invention. | |
| 1-1 | Paragraph number | 0013 |
| 1-3 | Description of Deposition | IPOD |
| 1-3-1 | Name of depository organization | Incorporated Administrative |
| 1-3-2 | Address of depository organization | Agency National Institute of Technology |
| 1-3-3 | Date of deposition | and Evaluation, International Patent |
| 1-3-4 | Accession number | Organisms Depositary (NITE-IPOD) 2-5-8-120 Kazusakamatari, Kisarazushi, Chiba 292-0818 Japan Nov. 14, 2013 (14 Nov. 2013) IPOD FERM BP-18976 |
| 1-5 | Designated country | All of the designated countries |
| 2 | The description below relates to the microorganism or biological specimen described in the detailed description of the invention. | |
| 2-1 | Paragraph number | 0048 |
| 2-3 | Description of Deposition | IPOD Incorporated Administrative |
| 2-3-1 | Name of depository organization | Agency National Institute of Technology |
| 2-3-2 | Address of depository organization | and Evaluation, Patent Microorganisms |

|       |                   |                                      |
|-------|-------------------|--------------------------------------|
| 2-3-3 | Date of deposition | Depositary (NPMD)                   |
| 2-3-4 | Accession number  | 2-5-8-122 Kazusakamatari, Kisarazu shi, Chiba 292-0818 Japan |
|       |                   | Nov. 22, 2018 (22 Nov. 2018)         |
|       |                   | NPMD NITE BP-02830                   |
| -5    | Designated country | All of the designated countries      |

Receiving Office Entry Field

|       |                                                                  |   |
|-------|------------------------------------------------------------------|---|
| 0-4   | This sheet was received with an international application. (Yes/No) | ✓ |
| 0-4-1 | Authorized officer                                               | Tsuneo NAGAI |

International Bureau Entry Field

|       |                                                            |   |
|-------|------------------------------------------------------------|---|
| 0-5   | Date when this sheet was received by the international bureau | |
| 0-5-1 | Authorized officer                                         |   |

The invention claimed is:

1. A coryneform bacterium transformant selected from the group consisting of:
 (a) a *Corynebacterium glutamicum* transformant obtained by introducing a gene that encodes an enzyme having phenylpyruvate decarboxylase activity into a *Corynebacterium glutanicum* in such a manner that the gene can be expressed, wherein the gene that encodes an enzyme having phenylpyruvate decarboxylase activity is a gene comprising a sequence having at least 98% identity to SEQ ID NO: 2;
 (b) a coryneform bacterium transformant obtained by introducing a plasmid having a gene that encodes an enzyme having phenylpyruvate decarboxylase activity into a coryneform bacterium in such a manner that the gene can be expressed, wherein the gene that encodes an enzyme having phenylpyruvate decarboxylase activity is a gene comprising a sequence having at least 98% identity to SEQ ID NO: 2; and
 (c) a coryneform bacterium transformant obtained by introducing a gene that encodes an enzyme having phenylpyruvate decarboxylase activity into a coryneform bacterium in such a manner that the gene can be expressed, wherein the gene that encodes an enzyme having phenylpyruvate decarboxylase activity is a gene comprising the sequence of SEQ ID NO:3.

2. The coryneform bacterium transformant according to claim 1,
 wherein the gene that encodes an enzyme having phenylpyruvate decarboxylase activity is an *Enterobacter cloacae* ipdC gene.

3. The the coryneform bacterium transformant according to claim 1,
 wherein the coryneform bacterium transformant is transformed with at least one gene selected from the group consisting of:
 a first gene that encodes an enzyme having 3-deoxy-D-arabino-heptulosonate-7-phosphate (DAHP) synthase activity;
 a second gene that encodes an enzyme having chorismate mutase activity and/or prephenate dehydrogenase activity; and
 a third gene that encodes an enzyme having shikimate kinase activity.

4. The coryneform bacterium transformant according to claim 3, wherein each of the first and second genes is a gene that encodes an enzyme having feedback inhibition resistance.

5. The coryneform bacterium transformant according to claim 3,
 wherein the first, second and third genes are *Escherichia coli* genes.

6. The coryneform bacterium transformant according to claim 1,
 wherein at least one gene selected from the group consisting of a lactate dehydrogenase gene, a 3-dehydroshikimate dehydratase gene, a dihydroxyacetone phosphatase gene, and a phenylalanine uptake transporter gene, is disrupted.

7. The coryneform bacterium transformant according to claim 1, wherein the coryneform bacterium transformanet of (b) or (c) is *Corynebacterium glutamicum*.

8. The coryneform bacterium transformant according to claim 1, wherein the *Corynebacterium glutamicum* of (a), the coryneform bacterium of (b) and the coryneform bacterium of (c) are *Corynebacterium glutamicum* R (FERM BP-18976), ATCC13032, or ATCC13869 (DSM1412).

9. A *Corynebacterium glutamicum* strain 2PE97 deposited under Accession Number: NITE BP-02830.

10. A method for producint 2-phenylethanol comprising culturing the coryneform bacterium transformant according to claim 1 in a medium containing a saccharide.

11. The method according to claim 10,
 wherein the saccharide is selected from the group consisting of glucose, fructose, mannose, xylose, arabinose, galactose, sucrose, maltose, lactose, cellobiose, xylobiose, trehalose, and mannitol.

12. The coryneform bacterium transformant according to claim 1, wherein the gene that encodes an enzyme having phenylpyruvate decarboxylase activity is a *Corynebacterium aurimucosum* pyruvate decarboxylase gene.

13. The coryneform bacterium transformant according to claim 1, wherein the gene that encodes an enzyme having phenylpyruvate decarboxylase activity is an *Enterobacter cloacae* ipdC gene that has the sequence of SEQ ID NO: 3.

14. The coryneform bacterium transformanet according to claim 2, wherein the coryneform bacterium transformant of (b) or (c) is *Corynebacterium glutamicum*.

15. The coryneform bacterium transformant according to claim 13, wherein the coryneform bacterium transformant of (c) is *Corynebacterium glutamicum*.

16. The coryneform bacterium transformant according to claim 1, wherein the transformant has 2-phenylethanol producing ability.

17. The coryneform bacterium transformant according to claim 13, wherein the transformant has 2-phenylethanol producing ability.

18. The coryneform bacterium transformant according to claim 1, wherein the gene that encodes an enzyme having phenylpyruvate decarboxylase activity is a gene comprising a sequence having at least 98% identity to SEQ ID NO: 2.

19. The coryneform bacterium transformant according to claim 1, wherein the gene that encodes an enzyme having phenylpyruvate decarboxylase activity is a gene comprising the sequence of SEQ ID NO: 2.

20. The coryneform bacterium transformant according to claim 1, wherein the gene that encodes an enzyme having phenylpyruvate decarboxylase activity is a gene comprising the sequence of SEQ ID NO: 3.

21. The coryneform bactrium transformant according to claim 1, wherein the coryneform bacterium transformant is the *Corynebacterium glutamicum* transformant obtained by introducing a gene that encodes an enzyme having phenylpyruvate decarboxylase activity into a *Corynebacterium glutamicum* in such a manner that the gene can be expressed, wherein the gene that encodes an enzyme hvaing phenylpyruvate decarboxylase activity is a gene comprising a sequence haveing at least 98% identity to SEQ ID NO: 2.

22. The coryneform bacterium transformant according to claim 1, wherein the coryneform bacterium transformant is the coryneform bacterium transformant obtained by introducing a plasmid having a gene that encodes an enzyme having phenylpyruvate decarboxylase activity into a coryneform bacterium in such a manner that the gene can be expressed, wherein the gene that encodes an enzyme having phenylpyruvate decarboxylase activity is a gene comprising a sequence having at least 98% identify to SEQ ID NO: 2.

23. The coryneform bacterium transformant according to claim 1, wherein the coryneform bacterium transformant is the coryneform bacterium transformant obtained by introducing a gene that encodes an enzyme having phenylpyruvate decarboxylase activity into a coryneform bacterium in such a manner that the gene can be expressed, wherein the gene that encodes an enzyme having phenylpyruvate decarboxylase activity is a gene comprising the sequence of SEQ ID NO: 3.

* * * * *

SEQUENCE LISTING

<160> NUMBER OF SEQ ID NOS: 39

<210> SEQ ID NO 1
<211> LENGTH: 1638
<212> TYPE: DNA
<213> ORGANISM: Azospirillum brasilense

<400> SEQUENCE: 1

```
atgaagctgg ccgaagcctt gctgcgcgcg ctgaaggatc gcggcgcaca ggccatgttc        60
gggattccgg gcgatttcgc cttgcccttc ttcaaggtgg cggaggaaac gcagatcctg       120
ccgctccaca cgctgagcca cgagccggcg gtgggcttcg cggcggacgc ggcggcgcgc       180
tacagctcca ctctaggggt ggcggcggtc acctacgggg cgggcgcctt caacatggtg       240
aatgcggtgg ccggcgccta cgccgagaag tcgccggtcg tcgtcatctc cggcgcgccg       300
ggcacgacgg agggcaacgc cggcctgctg ctgcaccacc agggccgcac gctggacacg       360
cagttccagg tgttcaagga gatcaccgtg gcccaggccc ggctggacga cccggccaag       420
gccccggcgg agatcgcccg cgtgctgggg gccgcccgcg ccctgtcgcg cccggtctat       480
ctggaaatcc cccgcaacat ggtcaacgcc gaggtcgagc cggtgggcga cgaccccgcc       540
tggccggtgg accgcgacgc gctggccgcc tgcgcggacg aggtgctggc ggccatgcgc       600
tcggccacgt ccccggtgct gatggtctgc gtcgaggtcc gccgctacgg gctggaggcc       660
aaggtggcgg agctggcgca gcggctgggc gtgccggtgg tcaccacctt catgggcgc        720 ggcctgctgg ccgacgcgcc gaccccgccg ctcggcacct acatcggcgt tgccggcgac       780
gcggagatca cccggctggt cgaggagtcg gacgggctgt tcctgctcgg cgccatcctc       840
agcgacacaa acttcgcggt gtcccagcgc aagatcgacc tgcgcaagac catccacgcc       900
ttcgaccggg cggtgacgct gggctatcac acctacgccg acatcccgct ggacgggctg       960
gtggacgcgc tgctggagcg gctgccgccg tccgaccgca cgacgcgcgg caaggaaccc      1020
cacgcctacc cgaccggcct tcaggccgac gacgccccca tcgcaccgat ggacatcgcc      1080
cgcgccgtca acgaccgcgt gcgcgccggg caggagccgc tgctgatcgc ggcggacatg      1140
ggcgactgcc tgttcaccgc catggacatg atcgacgccg gctgatggc gccgggctat        1200 tacgcgggca tgggcttcgg cgtgccggcg ggcatcgggg cgcagtgcgt gtcgggcggc       1260
aagcgcatcc tgacggtggt cggcgacggc gccttccaga tgaccgggtg ggagcttggc      1320
```

| | |
|---|---|
| aactgccgac ggctgggcat cgaccccatc gtgatcctgt tcaacaacgc cagttgggag | 1380 |
| atgctgcgca ccttccagcc cgaatccgcc ttcaatgacc tggacgactg gcgcttcgcc | 1440 |
| gagatggcgg cgggcatggg cggcgacggt gtgcgtgtgc gcacgcgggc ggagctgaag | 1500 |
| gcggcgctgg acaaggcctt cgccacgcgc gggcgcttcc agctgatcga ggcgatgatc | 1560 |
| ccccgcggcg tgctgtccga cacgctggcc cgcttcgtcc aggggcagaa gcgcctgcac | 1620 |
| gccgcgcccc gggaataa | 1638 |

<210> SEQ ID NO 2
<211> LENGTH: 1674
<212> TYPE: DNA
<213> ORGANISM: Corynebacterium aurimucosum

<400> SEQUENCE: 2

| | |
|---|---|
| atgcagacca ccattggtga tttcatcctg gaccgcctca aggccatcgg cattactgaa | 60 |
| atcatcggcg tgcccggtga cttcaacctg agcttcctcg agcagattga ggcctccgag | 120 |
| ggaatccgct tcgtcggcgc ctgcaacgag ctcaacgctg cctatgccgc tgatggctat | 180 |
| gcccgccaga aggtgtgggc tgcctgctc accacctacg gcgtgggcga gctttccgcc | 240 |
| ctcaacggca tcgcgggtgc acgtgccgag cacgtcccgc tggtgtcgct ggcgggcgcg | 300 |
| ccgccgcagt atgcgaccga attcgctgg aacctgcacc actcgcttgc cgacggcgac | 360 |
| tttgccaaca tgctggattc ctttgcaccc ttcaccgagg tggccacgcg tgtgtccccc | 420 |
| atgaacgtag tcgaggaatt cgaccgcgcc ctgcacacct gcctgcgcga agcgcccg | 480 |
| gtgcacatcc agattccttc cgatatcact cacctgacca tcgaggtccc cgacgaacct | 540 |
| ttctccaccg agctggcacc ctccgatcca gagcgcctga cgccgctgc ggactacgtg | 600 |
| ctggagcacc tcgctaaggc caaggacccg atcatcctca tcgaccagga caccaaccgc | 660 |
| cacggtttca cggagaaatt ccgcgccatc atcgacaagg cccagctgcc ctactcccag | 720 |
| ctctcctccg gcaaggccat cctgtctgag cgccacccgc tgttcatcgg cacctataac | 780 |
| ggcgcggcct ctgccccggg cgtgcaggag cgcatcgaaa atccgacttt cctggtcacc | 840 |
| accaaccccc gcttcatcga ggtcaactcc ggttccttca cccacaaacct ggccgatgcc | 900 |
| cgcgtctaca acttcggcga ccagcaccctc aacgccgacg gcgaatactt cgtgggcatc | 960 |
| aatacgctgg agcttctcga cgtcctcctc gaccgcatcc cggaagccgg ggcatcgaca | 1020 |
| agcgcggctt cgaacccga gcccttcgag ccgaacccgg atgccccgct gacccaggaa | 1080 |
| cgcatctggc gcagatgct cggcttcatc caagaagatg acgtggtcat cgccgaagcc | 1140 |
| ggcacctcca atatcggttt ggccagcag cgcatgcccg agggcgtgca gtacatcaac | 1200 |
| tccaccatct ggggttccat cggctttacc ctgccgtgcg tgctcggctc gcagctggcc | 1260 |
| aacccggagc gccgccacgt cctcttcatc ggtgatggct ccttccagct caccgcccag | 1320 |
| gagctgtcca ccatcctgcg ccaggacctc aagcccatca tcgtgctggt caataacgat | 1380 |
| ggctacacca tcgagcgcta catcttgggc atggagcgcg agtacaacga gatccagatg | 1440 |
| tgggattaca cgtctctgcc gaaggtcttc atgaaggaca ccacgatgga atcctacgtg | 1500 |
| gcctcaaccg aaggcgagct ggcgaaggcc ctagacgaca tcgctgccca cccagagcgc | 1560 |
| ggcgccttcc tcgaggttcg cctcgacgct ttcgacgcgc cgaagggcct tcaggccttc | 1620 |
| ggcccgcaga ccgctgattt cgacttcggc cctcgcggcc cccgcaacgc ctaa | 1674 |

<210> SEQ ID NO 3
<211> LENGTH: 1659

```
<212> TYPE: DNA
<213> ORGANISM: Enterobacter cloacae

<400> SEQUENCE: 3
atgcgaaccc catactgcgt cgccgattac ctgctggacc gtcttacaga ttgtggtgcc     60
gatcatctgt ttggcgtgcc gggcgactat aacctgcagt ttctcgatca tgtcatcgac    120
agcccggata tctgttgggt gggctgtgcc aatgagctaa acgcatctta tgccgctgac    180
ggatatgccc gatgtaaggg ctttgccgcg ctgctgacaa catttggcgt aggggaatta    240
agtgccatga acggcatggc cggcagcttt gccgagcatg ttccggtgtt acacattgtg    300
ggggcaccgg gtacggcctc acagcaaaaa ggtgagctgc tgcaccacac gctgggtgat    360
ggtgagttcc gtcacttcta ccatatgagt gaaccgatca cggtcgcgca ggcgatcctg    420
accgaacaaa acgcctgcta cgaaatcgac agagtgttaa caaccatgct gcgggagcga    480
cgtccaggct acctgatgct gcctgctgat gtggctaaaa aatcagccac gccgcctgta    540
aacgctctca cgttaaagac agcgcatgcc gataacgcct gcctgaaagc gttccgagac    600
gccgccgaga gcagactgaa acaagcaag cgtaccgcgc tgttggccga tttcctggtc    660
ctgcgccacg gcatgaaaca tgccctgcag aaatgggtga agaggtgcc cattgcccac    720 gccaccatgc tgatgggcaa gggcattttt gacgaacgcc agcccggttt ttatggcacg    780
tacagtggtt cggcaagcgt cggggcggta aagaggcca tcgaaggggc ggatacggta    840
ctgtgcattg gcacgcgttt tactgatact ctgacggcgg ggtttaccca tcagctgacg    900
caggcgcaaa cgatagaagt gcagccccat gccgcacggg tggggatgt ctggtttacc    960 ggtatcccta tgtctgacgc gatcgagacg ctggtggctc tctgcaaaca gtatgtccat   1020 gatccctgg cgccagtctc tcacagcggt atcgccttcc cgcaatccga gggctcgctc    1080
actcaggaga atttctggag caccctgcaa acctttattc gcccgggtga cattattctt   1140
gccgaccagg ggacgtcagc ctttggtgcg atcgatttgc gtctaccggc agatgtgaat   1200
tttatcgtcc agccgctgtg gggctccatt ggctacaccc tggccgcggc gtatggtgcc   1260
caaaccgcct gtccagaccg gcgcgtcatt gtgctcacgg gggatggcgc cgcgcagttg   1320
accattcagg aactgggctc gatgctgcgt gataaacagc accccattat cctggtgctc   1380
aacaatgaag ggtacaccgt agagagggcc attcatggac cggaacagcg ctataacgac   1440
attgccttat ggaactggac gcaaattccg caggcactga gcctggatcc tcaggcacag   1500
tgctggcggg tcagtgaagc ggaacagctg gcggaggtgc tcgaaaaagt ggcacaccac   1560
gagcgactaa cattgattga agtgatgcta cccaaagcgg atatcccgcc gctgttaggg   1620
gcgattacca aagcgctgga agcgtgtaat aacgcctga                          1659

<210> SEQ ID NO 4
<211> LENGTH: 1632
<212> TYPE: DNA
<213> ORGANISM: Rhodopseudomonas palustris

<400> SEQUENCE: 4
atgccgacac ttgcgaccgc gctgctcgac gccctcaagg atcatggtgc ccgagagatt     60
ttcggcattc ccggcgattt cgtgctgccg ttttttcaagg tgatcgaaga gagcggcacg    120
ctgccgtatt tcaccatgag ccacgagccg gcggtcggct tcgcggccga tgcggcgtcg    180
cgctatcgcg gcagcatcgg cgtcgcggtg gtgacctacg gggccggcgc gttcaacctc    240
gtcaactcga ttgccggcgc ctatgcggag cgctcgccgg tggtggtgat cgccggcgcg    300
```

```
ccgggcgcgc gcgagcgcac cagcggctat ctgctgcatc atcaggtccg caccgtcgat     360
tcccaactcg cggtattcaa ggaagtcact tgcgatcagg ccgtgctgag cgatccggcg     420
accgcgcccg cggagatcgc gcgggtgctg cggagcgcgc tcgaattgtc gctgccggtg     480
tacatcgaat ttccccgcga catggtcgac gccaaggtcg acccgtgcc gaagctgccg      540 cggcgcgagg ccgatatcgg cgcgcgggac gagtgtgccg aagaaatcct ggatcggatc     600
gccagggcaa agtcgccggt gatggtggtg gacgtcgaaa tccgccgcta cggcgtcgag     660
cagcaggtcg ccgcgctggc ccgcaagctc ggcctgccgg tggtgacgac gttcatgggc     720
cgcggcctgc tcaaggcga cgacgacgtg gtggctggca cctatctcgg cgcggctggt     780
gatccggacc tgtcggcgct ggtcgagggc gccgatctgg tgctgatgtt cggtgtcatc     840
ctgtccgata ccaacttcgc gctgtcctcg aacatgaccg atccgcgccg caccgtgctg     900
gcgactgggc gcgaggtgca gatcggccac cacgtctatc gcgacctgcc gctggctgac     960
ctgatcgccg gtctcgatgc ccacgcctcg cagcatccac cgcggccgcg caatgtcggt    1020
aaggggatgg cctatccgcg tgggctgacg ctcgacgcgt cgccgatcgc accgtcggat    1080
atcgccaccg cgatcaacga tctgttcgac cgccacggca agatgccgat gaccgccgat    1140 atcgcgatt gcctgttcac cgcgatggag atcgacaaca ctgcgctggc ggccccggga    1200
tactacgcag gcatggggtt cggcgtgccc gccggcgtcg gcgttgccgc gaccggcctg    1260
cggccgctgg tgctggtggg cgacggtgcg tttcagatga ccggctggga gctcggcaac    1320
tgcaagcgct acgggctcga tccgatcgtg gtgctgttca caattgcag ctgggaaatg     1380 ctgcgggtgt tccagccgga atccaagttc aacgatctgg acgactggca ctttgccgac    1440
atcgcgcatt cgatcggcgg cttcggcgag cgggtgacga cgcgcgccga actcgccgcg    1500
gcgctgcagc gcgcggtcga gcggcgcggg gtgttctcac tgatcgaagt gatgttgccg    1560
cgtggcgtta cctcgcacac gctggcgcgg ttcgtcaccg gcttcaaggc ggcgcgtgaa    1620
cggatgaagt ga                                                          1632

<210> SEQ ID NO 5
<211> LENGTH: 1662
<212> TYPE: DNA
<213> ORGANISM: Rhodospirillum rubrum

<400> SEQUENCE: 5
atgcccacca tcgccacggc cttgcttgac gcgttgaagg cccatggggc gacccggatc      60
ttcggcattc ccgcgatttt cgccctgccg ttcttccggg tggccgaaca aagcgccctc     120
ttgccgctgt acaccctgag ccacgaaccc ggagtcggct tcgccgccga cgcctgcgcc     180
cgcatggggc gcggcctcgg ggtggcgcg gtcacttacg gcgccggggc cttgaacatg      240
gtcaatccgg tggccggggc ttggtcggag aaatcacccc tggtggtgat tccggcgcc      300 cccgcgtcg ccgaatccgc cggcggcctg ctgctccacc atcaggccaa aaccctcgac     360
agccagtggc ggatctttga agagatcacc tgcgcccgca cccgccttga tgaccccgctg    420 accgccccg gggaaatcgc ccgggtgttg cgggcctgcc ttgaacactc ccgcccgtc      480 tatatcgaaa tccccgcga catcgtcgat gcgccctgcg ccgccgtgga ccgcctgccg     540
cccaccccgg tcgatggcga agcggtcgaa gccgccgccg gcgagatcat ggcccgcttg    600
gctgcggcca gcgccccggc gctgctgctg ggggtcgagg tccgtcgcca ggcatcgaa     660 gccgatgtcg ccgaactggc ccgccgcctg ggcctgccca tcgccaccac cttcatgggc    720
cggggtctgt tatccgagga gggcgcggcc ggcggcgcgc ccgacagcct gatgggcacc    780
```

```
tatctggggc tggccggccg ccccgaggtg cgcgccgtca tcgaagactc cgatggcctg      840
ctgatgctcg gcgtcatctt gtccgacacc aatttcggcg tttcgggcaa gcgcatcgac      900
ctgcgccgcg ccatgctcgc cgccgaccgt caggtcgccc tgggctttca tacctataac      960
gatatcccgc tggccgatct ggtcgccgcc ctgctgcgtc aggccgaggg cttcgcccgc     1020
caggacgcca aggccctacc caagccgacc gccctgcccc gggacatgat cgccgatggg     1080
gcgccgatcg gcccgatgga tatcgccgcg ccatcaacg atctattctc ggcccatggg      1140
gtgatgccga tcgcctcgga tatgggcgat tgcctgttca ccgcccttga taccacccat     1200
gcgccgctgg tcgcccccgggg ctattacgcc accatgggct ttggcgtgcc ggcgggattg   1260
ggcgttcagg ccagctgtgg ccgccggccg ctgatcctgg tcggcgacgg cgcctttcag     1320
atgaccggtt gggagttggg caattgcgcc cgctacggct gggacccgat cgtcatcgtc     1380
ttcaacaacg ccagttggga gatgctgcgc accttccaac ccgacaccgc ctataacgat     1440
ctggccgatt ggcgattcgc cgatctggcc gccggcctgg gcggcgttgg tcaccgttgc     1500
caaacccgcg ccgatctggc ccgggccctg gatcgggcgg cccgcgaacc ggggcgcttt     1560
cacctgatcg aggcggttct ggcgcgcggg gcgatctcgg acaccctcca gcgcttcgtc     1620
accacgatga aggccgcca cgccgcggcg gccgatgcct ga                         1662

<210> SEQ ID NO 6
<211> LENGTH: 525
<212> TYPE: DNA
<213> ORGANISM: Escherichia coli

<400> SEQUENCE: 6
atgacacaac ctcttttttct gatcgggcct cggggctgtg gtaaaacaac ggtcggaatg      60 gccccttgccg attcgcttaa ccgtcggttt gtcgataccg atcagtggtt gcaatcacag     120
ctcaatatga cggtcgcgga gatcgtcgaa agggaagagt gggcgggatt tcgcgccaga     180
gaaacggcgg cgctggaagc ggtaactgcg ccatccaccg ttatcgctac aggcggcggc     240
attattctga cggaatttaa tcgtcacttc atgcaaaata cgggatcgt ggtttatttg      300 tgtgcgccag tatcagtcct ggttaaccga ctgcaagctg caccggaaga agatttacgg     360
ccaaccttaa cgggaaaaacc gctgagcgaa gaagttcagg aagtgctgga gaacgcgat    420 gcgctatatc gcgaagttgc gcatattatc atcgacgcaa caaacgaacc cagccaggtg    480
atttctgaaa ttcgcagcgc cctggcacag acgatcaatt gttga                    525

<210> SEQ ID NO 7
<211> LENGTH: 1155
<212> TYPE: DNA
<213> ORGANISM: Escherichia coli

<400> SEQUENCE: 7
atgacatcgg aaaacccgtt actggcgctg cgagagaaaa tcagcgcgct ggatgaaaaa      60
ttattagcgt tactggcaga acggcgcgaa ctggccgtcg aggtgggaaa agccaaactg     120
ctctcgcatc gcccggtacg tgatattgat cgtgaacgcg atttgctgga agattaatt     180 acgctcggta aagcgcacca tctggacgcc cattacatta tcgcctgtt ccagctcatc     240 attgaagatt ccgtattaac tcagcaggct ttgctccaac aacatctcaa taaaattaat    300
ccgcactcag cacgcatcgc tttttctcggc cccaaaggtt cttattccca tcttgcggcg    360
cgccagtatg ctgcccgtca ctttgagcaa ttcattgaaa gtggctgcgc caaatttgcc    420
```

```
gatattttta atcaggtgga aaccggccag gccgactatg ccgtcgtacc gattgaaaat    480
accagctccg gtgccataaa cgacgtttac gatctgctgc aacataccag cttgtcgatt    540
gttggcgaga tgacgttaac tatcgaccat tgtttgttgg tctccggcac tactgattta    600
tccaccatca atacggtcta cagccatccg cagccattcc agcaatgcag caaattcctt    660
aatcgttatc cgcactggaa gattgaatat accgaaagta cgtctgcggc aatggaaaag    720
gttgcacagg caaaatcacc gcatgttgct gcgttgggaa gcgaagctgg cggcactttg    780
tacggtttgc aggtactgga gcgtattgaa gcaaatcagc gacaaaactt caccccgattt    840 gtggtgttgg cgcgtaaagc cattaacgtg tctgatcagg ttccggcgaa aaccacgttg    900
ttaatggcga agcaagccgg tgcgctggtt gaagcgttgc tggtactgcg caaccacaat    960
ctgattatga cccgtctgga atcacgcccg attcacggta atccatggga agagatgttc   1020
tatctggata ttcaggccaa tcttgaatca gcggaaatgc aaaaagcatt gaaagagtta   1080
ggggaaatca cccgttcaat gaaggtattg ggctgttacc caagtgagaa cgtagtgcct   1140
gttgatccaa cctga                                                    1155

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
ggaattccat atgaagctgg ccgaagcc                                         28

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
ggaattccat atgttattcc cggggcgcgg                                       30

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
ctctcatatg cagaccacca ttggtg                                           26

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
ctctcatatg tctccacctt aggcgttg                                         28

<210> SEQ ID NO 12
<211> LENGTH: 30
<212> TYPE: DNA
<213> ORGANISM: Artificial Sequence
```

<220> FEATURE:
<223> OTHER INFORMATION: Primer

<400> SEQUENCE: 12
ctcttcgcga atgcgaaccc catactgcgt                                    30

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
ctcttcgcga tcaggcgtta ttacacgctt c                                  31

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ctctcatatg ccgacacttg cgac                                          24

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
ctctcatatg tcacttcatc cgttcacgc                                     29

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
ggaattccat atgcccacca tcgccacg                                      28

<210> SEQ ID NO 17
<211> LENGTH: 32
<212> TYPE: DNA
<213> ORGANISM: Artificial Sequence
<220> FEATURE:
<223> OTHER INFORMATION: Primer

<400> SEQUENCE: 17
ggaattccat atgcccgtcc ttgatcgaag gg                                 32

<210> SEQ ID NO 18
<211> LENGTH: 32
<212> TYPE: DNA
<213> ORGANISM: Artificial Sequence
<220> FEATURE:
<223> OTHER INFORMATION: Primer

<400> SEQUENCE: 18
ctctcatatg acacaacctc tttttctgat cg                                 32

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
ctctcatatg acgttaagta taggcgctcg                    30

<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20
ggaattccat atgacatcgg aaaacccgtt ac                 32

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
cgccattaac aacgtggttt tc                            22

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
aagcaagccg gtgcgctgg                                19

<210> SEQ ID NO 23
<211> LENGTH: 34
<212> TYPE: DNA
<213> ORGANISM: Artificial Sequence
<220> FEATURE:
<223> OTHER INFORMATION: Primer

<400> SEQUENCE: 23
ggaattccat atgtcaggtt ggatcaacag gcac               34

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
ctctgtcgac gagaccatat gcacgttgtc                    30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
ctctgtcgac gctgaatcta agggtgttgc					30

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
ctctcctgca ggggattgga tgactgagca c				31

<210> SEQ ID NO 27
<211> LENGTH: 32
<212> TYPE: DNA
<213> ORGANISM: Artificial Sequence
<220> FEATURE:
<223> OTHER INFORMATION: Primer

<400> SEQUENCE: 27
ctctcctgca ggctccatca ttaagcgacg ag				32

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
ctctgtcgac atggcgtcat cgacattggt					30

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
ctctgtcgac accttgcgag caactcaatc					30

<210> SEQ ID NO 30
<211> LENGTH: 33
<212> TYPE: DNA
<213> ORGANISM: Artificial Sequence
<220> FEATURE:
<223> OTHER INFORMATION: Primer

<400> SEQUENCE: 30
ctctagatct gaaaggtaag acactagtta ccg				33

<210> SEQ ID NO 31
<211> LENGTH: 32
<212> TYPE: DNA
<213> ORGANISM: Artificial Sequence
<220> FEATURE:
<223> OTHER INFORMATION: Primer

<400> SEQUENCE: 31
ctctagatct atctgcatgg tttcagacaa cc				32

<210> SEQ ID NO 32

<210> SEQ ID NO 32
<211> LENGTH: 32
<212> TYPE: DNA
<213> ORGANISM: Artificial Sequence
<220> FEATURE:
<223> OTHER INFORMATION: Primer

<400> SEQUENCE: 32
ctctgcatgc ctgaattact gagctcacct tg                                   32

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
agatcaatgg tggcgatctc                                                 20

<210> SEQ ID NO 34
<211> LENGTH: 41
<212> TYPE: DNA
<213> ORGANISM: Artificial Sequence
<220> FEATURE:
<223> OTHER INFORMATION: Primer

<400> SEQUENCE: 34
gagatcgcca ccattgatct gctggaacac atcaatgatg c                         41

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
ctcttctaga cccaactctg ttcttcgcag                                      30

<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36
ctctgcatgc gctagaccaa caacatcctg                                      30

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
cgatgaagtg aatgtgtcga g                                               21

<210> SEQ ID NO 38
<211> LENGTH: 40
<212> TYPE: DNA
<213> ORGANISM: Artificial Sequence
<220> FEATURE:
<223> OTHER INFORMATION: Primer

<400> SEQUENCE: 38

```
ctcgacacat tcacttcatc ggacaactac cacctgccac                               40

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39
ctcttctaga tcaactgcag agacagtcag                                         30
```